United States Patent
Keating

(10) Patent No.: US 11,173,248 B2
(45) Date of Patent: *Nov. 16, 2021

(54) METHOD AND SYSTEM FOR OPERATING A PLUNGER

(71) Applicant: Kellida Inc., Atlanta, GA (US)

(72) Inventor: Virginia Souris Keating, Atlanta, GA (US)

(73) Assignee: Kellida Inc., Atlanta, GA (US)

(*) Notice: Subject to any disclaimer, the term of this patent is extended or adjusted under 35 U.S.C. 154(b) by 203 days.

This patent is subject to a terminal disclaimer.

(21) Appl. No.: 16/392,458

(22) Filed: Apr. 23, 2019

(65) Prior Publication Data

US 2020/0206425 A1  Jul. 2, 2020

Related U.S. Application Data

(60) Provisional application No. 62/661,122, filed on Apr. 23, 2018.

(51) Int. Cl.
*A61M 5/31* (2006.01)

(52) U.S. Cl.
CPC ........ *A61M 5/3137* (2013.01); *A61M 5/3135* (2013.01); *A61M 5/3148* (2013.01); *A61M 2005/3139* (2013.01)

(58) Field of Classification Search
CPC ........ A61M 5/3137; A61M 2005/3139; A61M 31/002; A61M 5/00; A61M 5/3148; A61M 2205/586; A61B 18/1815
See application file for complete search history.

(56) References Cited

U.S. PATENT DOCUMENTS

| | | | |
|---|---|---|---|
| 1,339,282 A * | 5/1920 | Pelnar | A01D 45/026 30/232 |
| 1,775,562 A * | 9/1930 | Kerns | A01D 46/247 30/232 |
| 2,346,607 A | 4/1944 | Raiman | |
| 2,842,128 A * | 7/1958 | Hein, Jr. | A61M 5/31 604/227 |
| 3,758,006 A | 9/1973 | Gravlee | |
| D248,598 S | 7/1978 | Bahmer | |

(Continued)

FOREIGN PATENT DOCUMENTS

WO  9822166 A1  5/1998

OTHER PUBLICATIONS

EP 20170359.2, European Search Report dated Jun. 3, 2020, 8 pages.

(Continued)

*Primary Examiner* — Scott J Medway

(57) ABSTRACT

An apparatus can aid usage of a plunger, for example helping a medical practitioner use a hypodermic syringe to inject dermal filler. The apparatus can fasten a thumb rest of a plunger of the syringe to a thumb of the practitioner and can support one-handed operation of the syringe. With the plunger so fastened, reverse thumb motion can retract the plunger for aspiration, and forward thumb motion can advance the plunger for injection. The apparatus can comprise a member extending at least partially around the practitioner's thumb. The member can comprise an aperture configured to retain the thumb rest between the thumb and the member, with a shaft of the plunger passing through the aperture.

20 Claims, 11 Drawing Sheets

(56) References Cited

U.S. PATENT DOCUMENTS

| | | | |
|---|---|---|---|
| 4,217,896 A | 8/1980 | Behnke | |
| 4,324,241 A | 4/1982 | Reese | |
| 4,351,334 A | 9/1982 | Inglefield, Jr. | |
| 4,687,472 A | 8/1987 | Gross | |
| 5,046,381 A | 9/1991 | Mueller | |
| 5,129,888 A * | 7/1992 | Bidoia | A61M 5/347 |
| | | | 600/576 |
| D335,196 S | 4/1993 | Lamb et al. | |
| 5,554,132 A | 9/1996 | Straits et al. | |
| 5,556,092 A * | 9/1996 | Theken | A63B 60/10 |
| | | | 473/538 |
| D397,790 S | 9/1998 | Naganuma | |
| 5,833,668 A | 11/1998 | Aguilar | |
| 6,068,616 A | 5/2000 | Janus | |
| D434,850 S | 12/2000 | Balestracci | |
| 6,394,984 B1 * | 5/2002 | Hill | A61M 5/28 |
| | | | 604/218 |
| D465,306 S | 11/2002 | Price | |
| D504,635 S | 5/2005 | Jones | |
| 6,944,914 B2 | 9/2005 | Tillim | |
| D543,625 S | 5/2007 | Numata et al. | |
| 7,364,570 B2 | 4/2008 | Gerondale et al. | |
| D620,384 S | 7/2010 | Crovetti | |
| D675,317 S | 1/2013 | Baxter et al. | |
| D702,402 S | 4/2014 | Pew | |
| D750,768 S | 3/2016 | Davidian et al. | |
| D790,691 S | 6/2017 | Davis et al. | |
| D794,185 S | 8/2017 | Dolk et al. | |
| D794,187 S | 8/2017 | Dolk et al. | |
| D797,282 S | 9/2017 | Dolk et al. | |
| D811,589 S | 2/2018 | Finke et al. | |
| D812,223 S | 3/2018 | Evans et al. | |
| D814,630 S | 4/2018 | Finke et al. | |
| D823,836 S | 7/2018 | Eaton | |
| D830,220 S | 10/2018 | Hardy | |
| 10,124,238 B2 | 11/2018 | McCrane | |
| D842,751 S | 3/2019 | Hardy | |
| D844,776 S | 4/2019 | Combes et al. | |
| D865,950 S | 11/2019 | Mandaroux et al. | |
| D869,775 S | 12/2019 | Voosen | |
| 10,842,940 B1 * | 11/2020 | Pusateri | A61M 5/31511 |
| 2003/0028146 A1 | 2/2003 | Aves | |
| 2005/0209571 A1 * | 9/2005 | McKay | A61M 5/3148 |
| | | | 604/227 |
| 2005/0215958 A1 * | 9/2005 | Hawthorne | A61B 10/0283 |
| | | | 604/227 |
| 2006/0205526 A1 | 9/2006 | Whitehead et al. | |
| 2009/0093787 A1 | 4/2009 | Barbour | |
| 2012/0220948 A1 | 8/2012 | Barbour | |
| 2015/0238698 A1 | 8/2015 | Perry et al. | |
| 2016/0213570 A1 * | 7/2016 | Athanassiou | A61J 7/0053 |
| 2017/0119952 A1 * | 5/2017 | Wen | A61M 5/3137 |
| 2019/0030253 A1 | 1/2019 | Barbour | |
| 2020/0197603 A1 * | 6/2020 | Cowe | A61M 5/2053 |
| 2020/0206425 A1 | 7/2020 | Keating | |

OTHER PUBLICATIONS

Sibbitt et al., Thyroid Biopsy with the Reciprocating Procedure Device (RPD), 2006, 2007, 114 pages, University of Mew Mexico Health Sciences Center.

Notice of Allowance issued in U.S. Appl. No. 29/688,668, dated Jul. 29, 2020, 26 pages.

Miltex, Dental Syringes and Accessories, 2010, 6 pages, Integra LifeSciences Corporation (brochure).

Medestheticsmag.Com, Jan. 12, 2017, 1 page.

Angiographic Control Syringes, Namie Fluid Management, 2014, 4 pages, AngioDynamics, Inc.

Lee, Preventing Catastrophes—While Injecting Facial Wrinkles, Oct. 21, 2016, 2 pages, Press Advantage.

ProSystem Bionic Oxygen Recovery, Prime-Journal.com, Jul./Aug. 2017, 2 pages.

Jireis, The Best Guitar Finger Picks by Dunlop—Thumbpicks Included! Jan. 7, 2017, 2 pages.

Non-Final Office Action issued in U.S. Appl. No. 16/827,433, dated Jun. 23, 2020, 39 pages.

Non-Final Office Action issued in U.S. Appl. No. 16/827,433, dated Sep. 8, 2020, 24 pages.

* cited by examiner

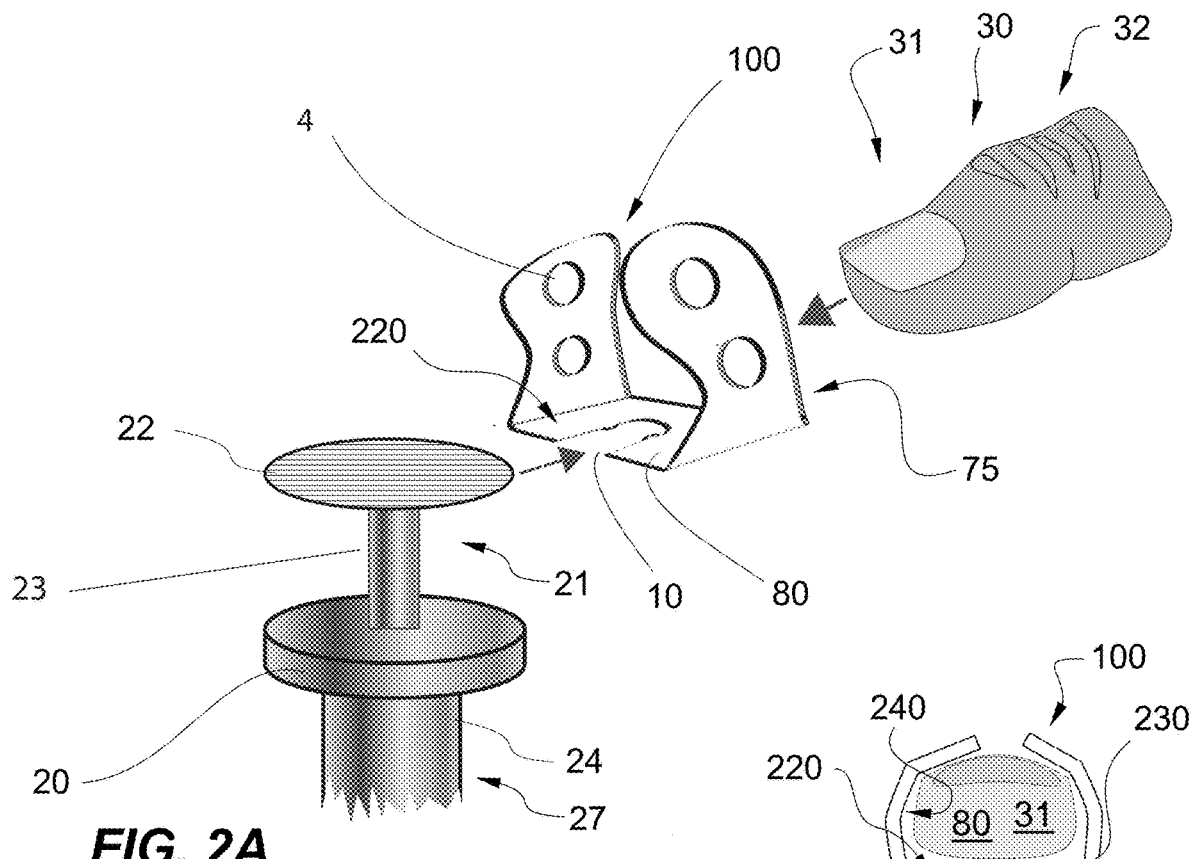
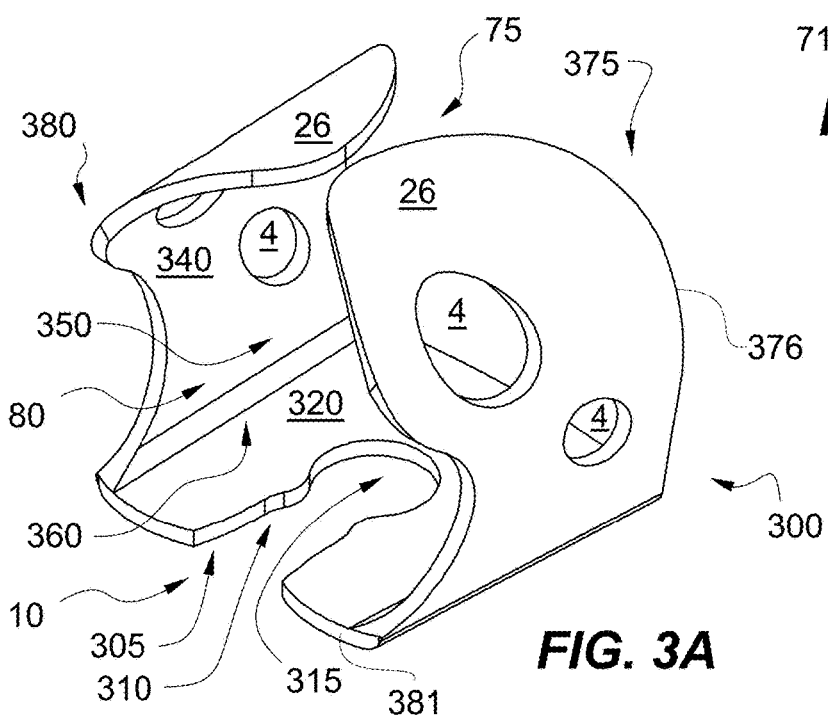

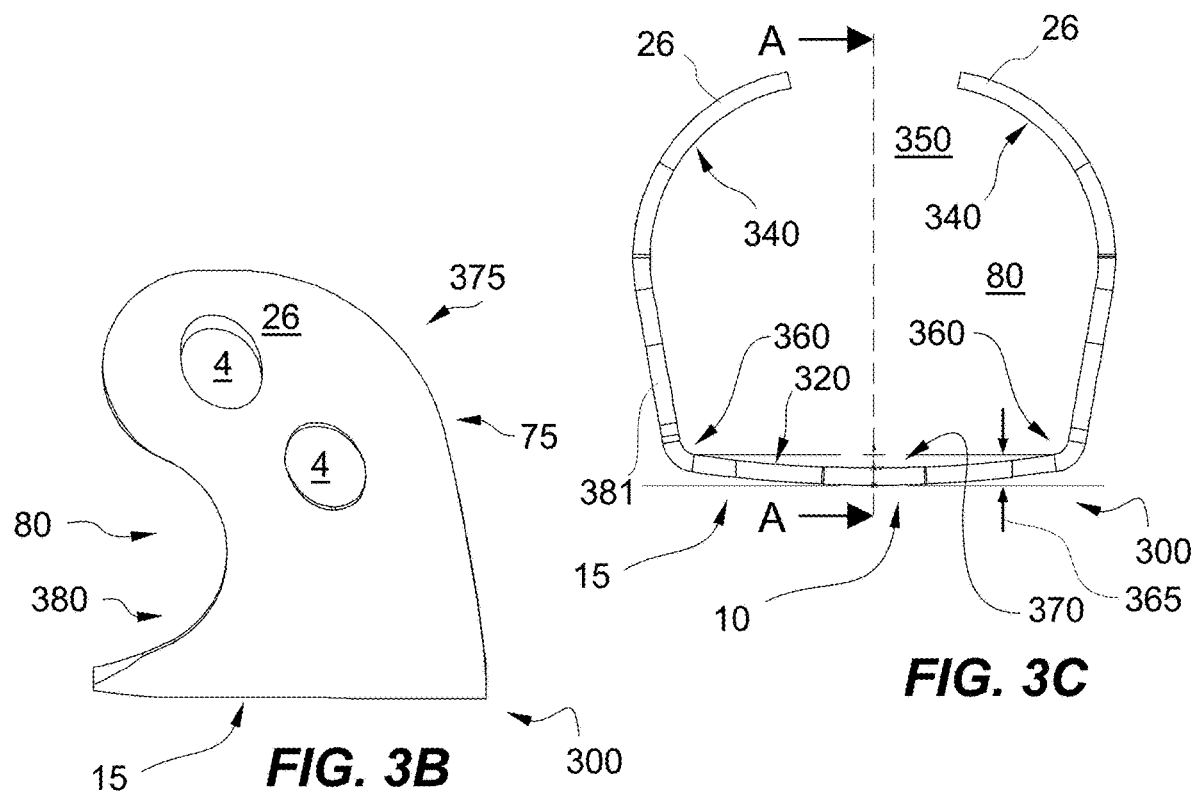
FIG. 3B
FIG. 3C
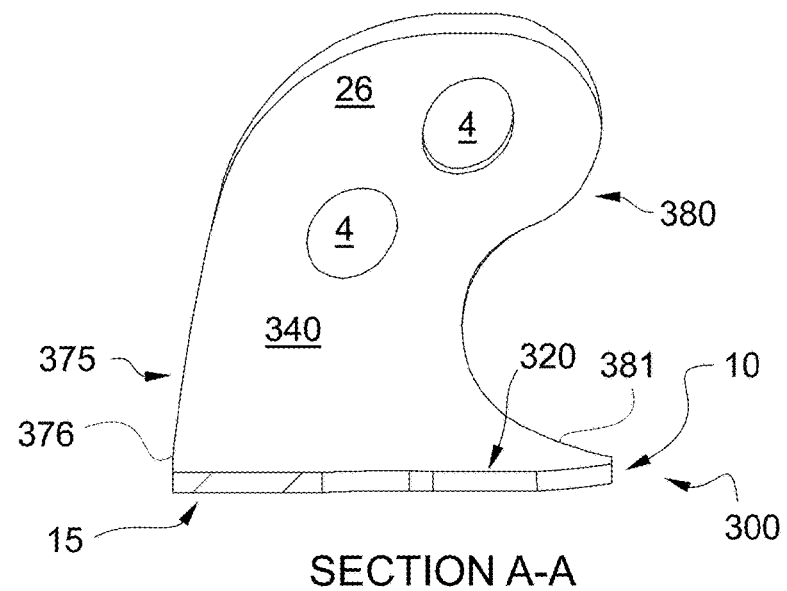
SECTION A-A
FIG. 3D

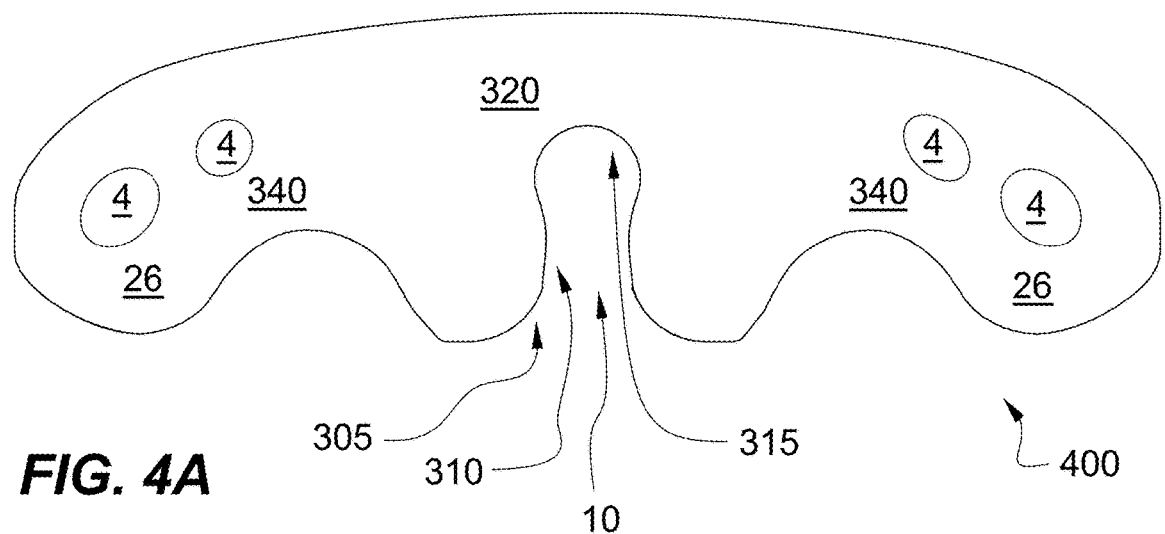
FIG. 4A
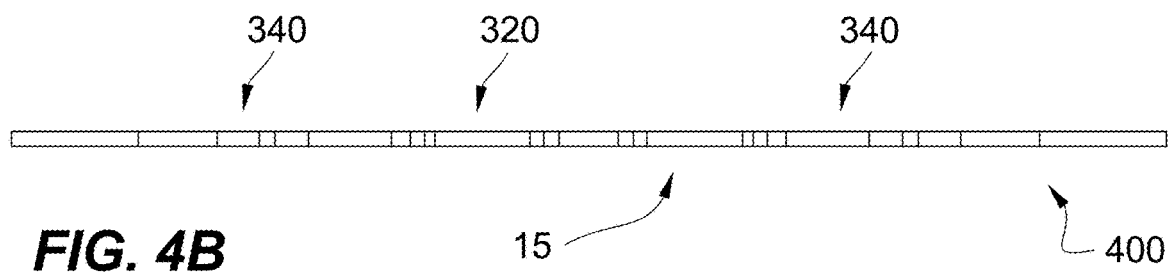
FIG. 4B
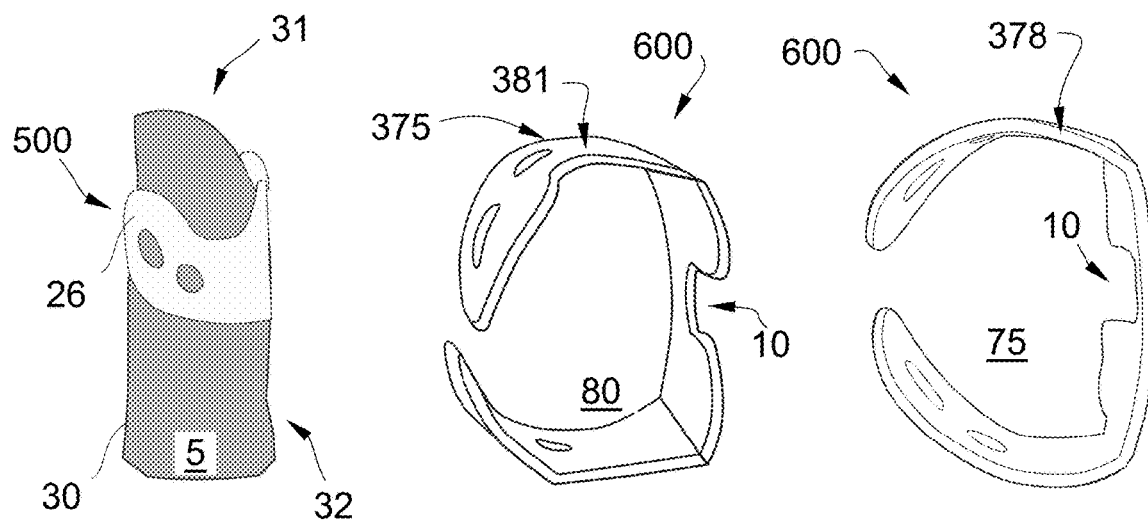
FIG. 5      FIG. 6A      FIG. 6B

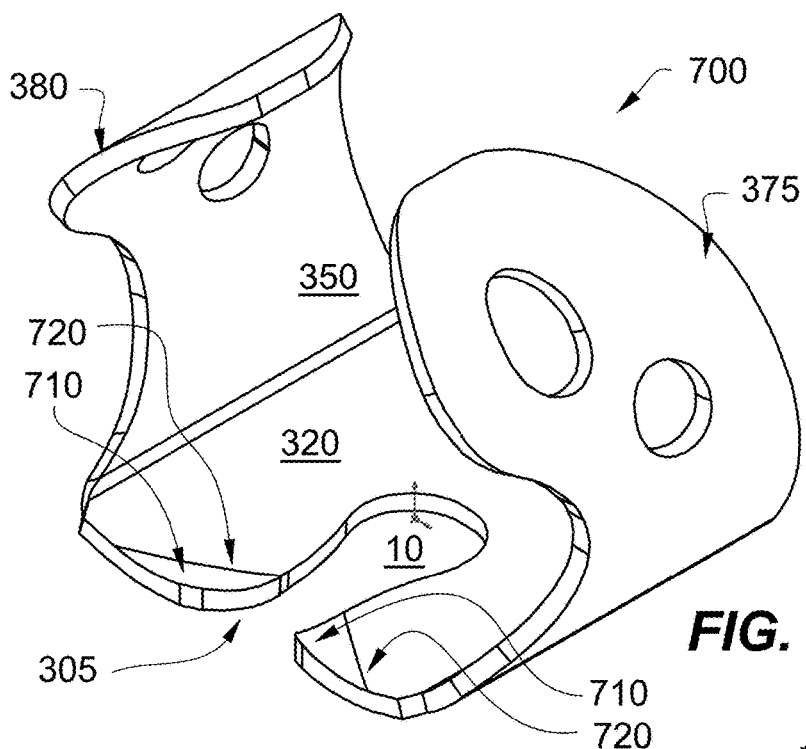
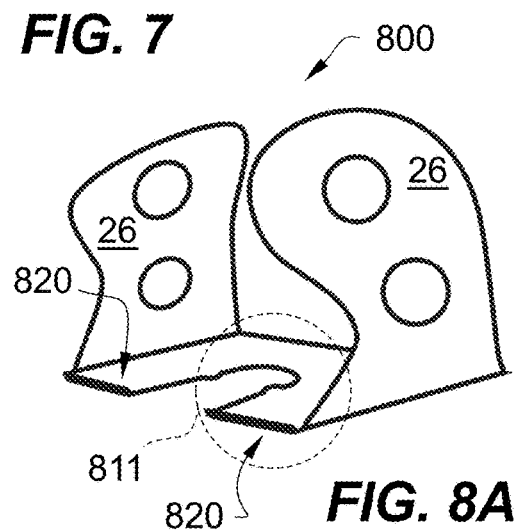
FIG. 7
FIG. 8A
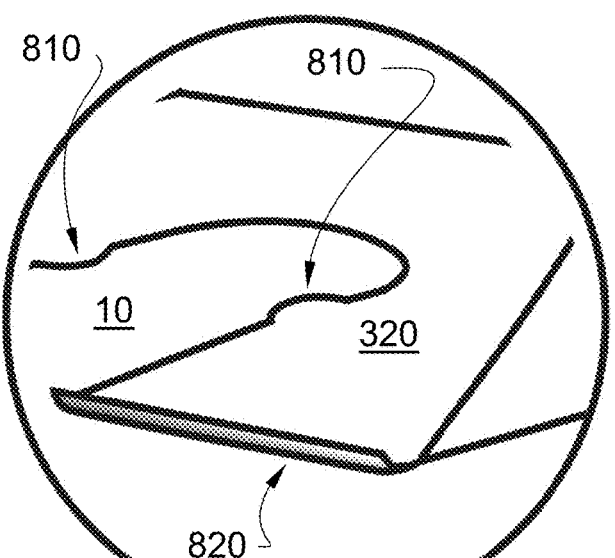
FIG. 8B
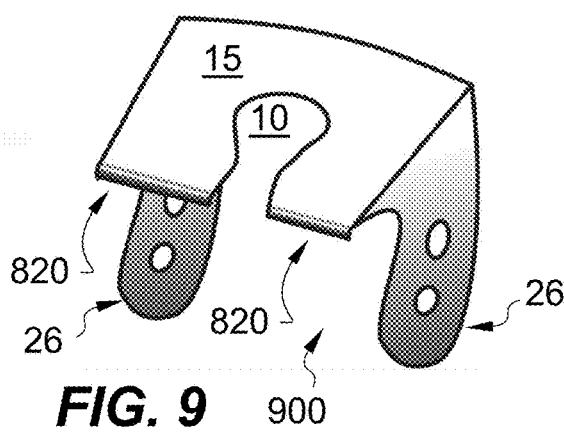
FIG. 9

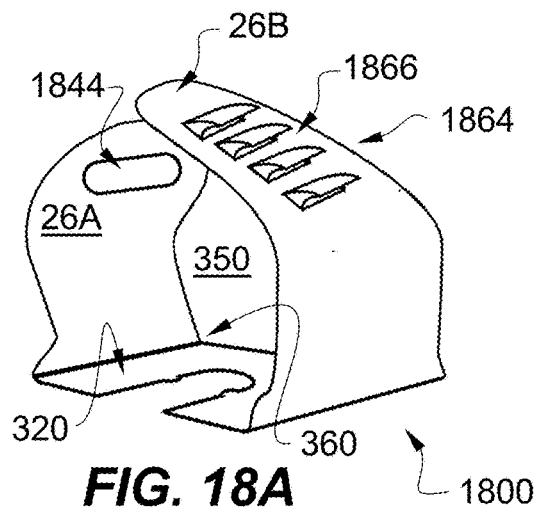
FIG. 18A
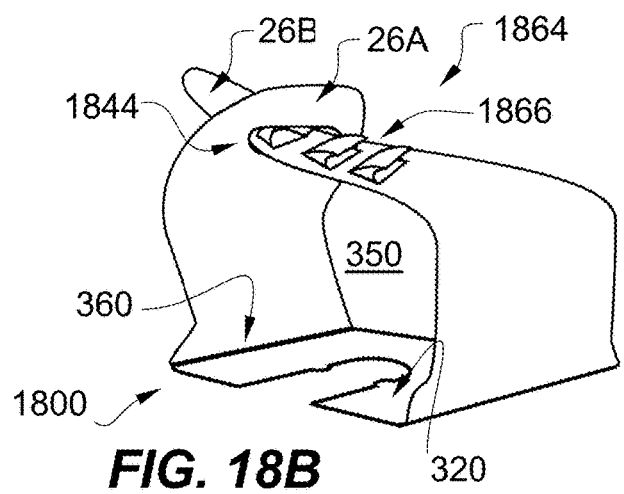
FIG. 18B
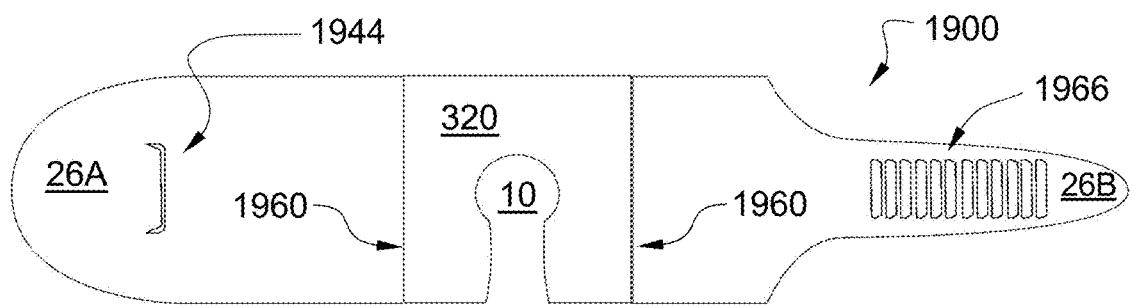
FIG. 19
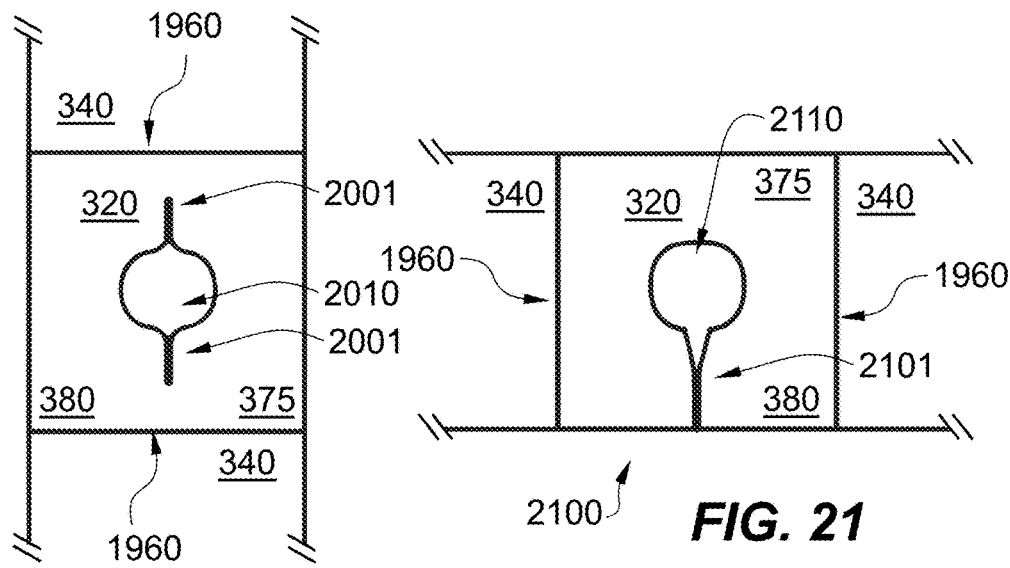
FIG. 20
FIG. 21

METHOD AND SYSTEM FOR OPERATING A PLUNGER

CROSS REFERENCE TO RELATED APPLICATIONS

This application claims priority to U.S. Provisional Patent Application No. 62/661,122 filed Apr. 23, 2018 in the name of Virginia Souris Keating and entitled "Novel Adjustable Clip-on Ring to Aid in Injection and Aspiration of a Syringe," the entire contents of which are hereby incorporated herein by reference. This application is related to U.S. Design Patent Application Number 29/688,668, filed on Apr. 23, 2019 in the name of Virginia Souris Keating and entitled "Plunger Fastening Device," now U.S. Pat. No. D903,112, the entire contents of which are hereby incorporated herein by reference. U.S. patent application Ser. No. 16/827,433, filed Mar. 23, 2020 in the name of Virginia Souris Keating and entitled "Method and System for Operating a Plunger," is a continuation of the present patent application and has been afforded an issue date of Apr. 13, 2021 as U.S. Pat. No. 10,973,982.

TECHNICAL FIELD

Embodiments of the technology relate generally to operating a plunger, and more specifically to fastening the plunger to a user to improve dexterity of operation, for example supporting precision retraction of a plunger of a hypodermic syringe in connection with aspirating the syringe.

BACKGROUND

Operators of devices that comprise plungers have often faced limitations in the level of precision with which they can move or position a plunger. For example, to achieve adequate plunger control using conventional approaches, an operator may find need to hold the device with one hand and retract the plunger with the other hand.

There is a deficiency in the art for technology for moving a plunger. Need exists for an improved capability to operate a plunger with precision. Need further exists for an improved capability to move a plunger manually with dexterity. Need further exists to improve retraction of plungers of medical instruments and tools. Need further exists to improve retraction of plungers of industrial instruments and tools. Need further exists for an improved capability for one-handed operation of a device that comprises a plunger. Need further exists for an improved capability for aspirating a hypodermic syringe or other medical device comprising a plunger. Need further exists for an improved capability for retracting a plunger of a biopsy instrument. A technology addressing one or more such needs, or a related deficiency in the art, could improve usage of devices incorporating plungers.

SUMMARY

A method and system can assist with moving a plunger, for example improving dexterity for someone using a device comprising a plunger. The device can comprise an industrial device or a medical device, such as a biopsy device, a surgical instrument, or a hypodermic syringe.

In one aspect of the disclosure, fastening a plunger to its user can increase dexterity or precision with which the user can retract the plunger.

In one aspect of the disclosure, fastening a plunger to a thumb or other appropriate appendage of a user can offer the user a capability for one-handed retraction of the plunger.

In one aspect of the disclosure, a plunger of a syringe can comprise a flange, for example a thumb rest. A user can apply force to the flange to advance the plunger. Advancing the plunger can cause material to emit from the syringe, for example in connection with a medical practitioner injecting a substance into a patient during a medical procedure. The flange can be fastened to an appendage of the user, for example to the user's thumb. With the flange so fastened, the user can retract the plunger with finesse, for example in support of performing an aspiration associated with a hypodermic injection or other procedure.

The foregoing discussion about moving a plunger is for illustrative purposes only. Various aspects of the present disclosure may be more clearly understood and appreciated from a review of the following text and by reference to the associated drawings and the claims that follow. Other aspects, systems, methods, features, advantages, and objects of the present disclosure will become apparent to those with skill in the art upon examination of the following drawings and text. It is intended that all such aspects, systems, methods, features, advantages, and objects are to be included within this description and covered by this paper and by the appended claims.

BRIEF DESCRIPTION OF THE FIGURES

FIG. 1, are illustrations of a ring for fastening a plunger to a user, with the ring illustrated in a representative medical application, in accordance with some example embodiments of the disclosure.

FIGS. 2A and 2B, collectively FIG. 2, are illustrations of a ring for fastening a plunger to a user, depicting representative features of fastening in accordance with some example embodiments of the disclosure.

FIGS. 3A, 3B, 3C, and 3D, collectively FIG. 3, are illustrations of a ring for fastening a plunger to a user in accordance with some example embodiments of the disclosure.

FIGS. 4A and 4B, collectively FIG. 4, are illustrations of a blank to be formed into a ring for fastening a plunger to a user in accordance with some example embodiments of the disclosure.

FIG. 5, is an illustration of a ring for fastening a plunger to a user, illustrated disposed on thumb, in accordance with some example embodiments of the disclosure.

FIGS. 6A and 6B, collectively FIG. 6, are illustrations of a ring for fastening a plunger to a user in accordance with some example embodiments of the disclosure.

FIG. 7 is an illustration of a ring for fastening a plunger to a user in accordance with some example embodiments of the disclosure.

FIGS. 8A and 8B, collectively FIG. 8, are illustrations of a ring for fastening a plunger to a user in accordance with some example embodiments of the disclosure.

FIG. 9 is an illustration of a ring for fastening a plunger to a user in accordance with some example embodiments of the disclosure.

FIG. 10, are illustrations of a ring for fastening a plunger to a user in accordance with some example embodiments of the disclosure.

FIGS. 18A and 18B, collectively FIG. 18, are illustrations of a ring for fastening a plunger to a user in accordance with some example embodiments of the disclosure.

FIG. 19 is an illustration of a ring for fastening a plunger to a user in accordance with some example embodiments of the disclosure.

FIG. 20 is an illustration of a portion of a ring for fastening a plunger to a user in accordance with some example embodiments of the disclosure.

FIG. 21 is an illustration of a portion of a ring for fastening a plunger to a user in accordance with some example embodiments of the disclosure.

FIG. 23, are illustrations of a ring for fastening a plunger to a user in accordance with some example embodiments of the disclosure.

Figure 1A:
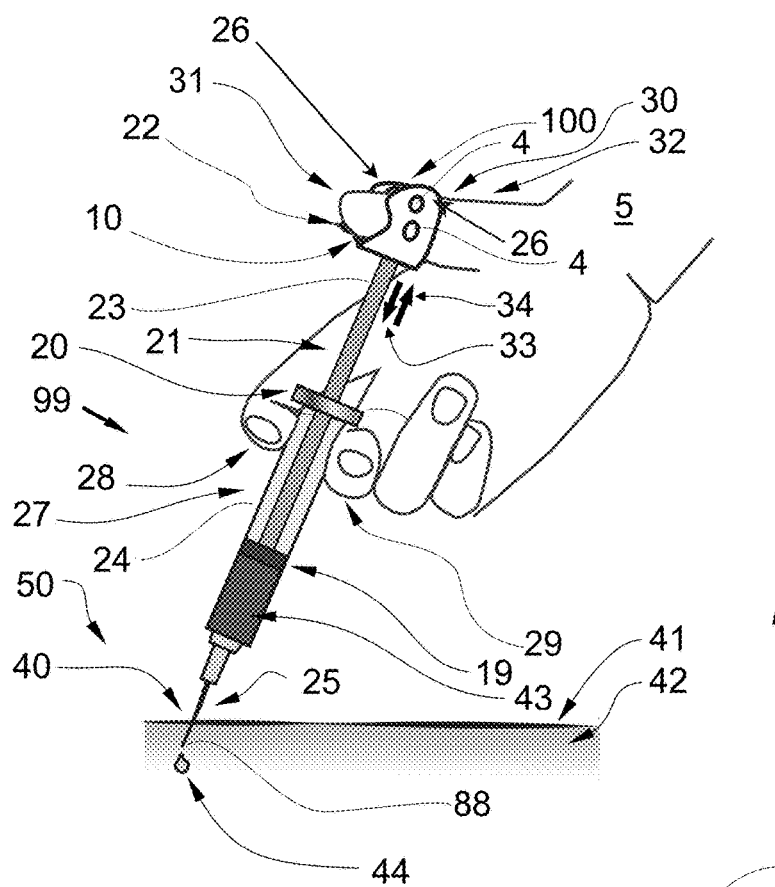
FIGS. 1A, 1B, 1C, and 1D, collectively
Figure 1B:
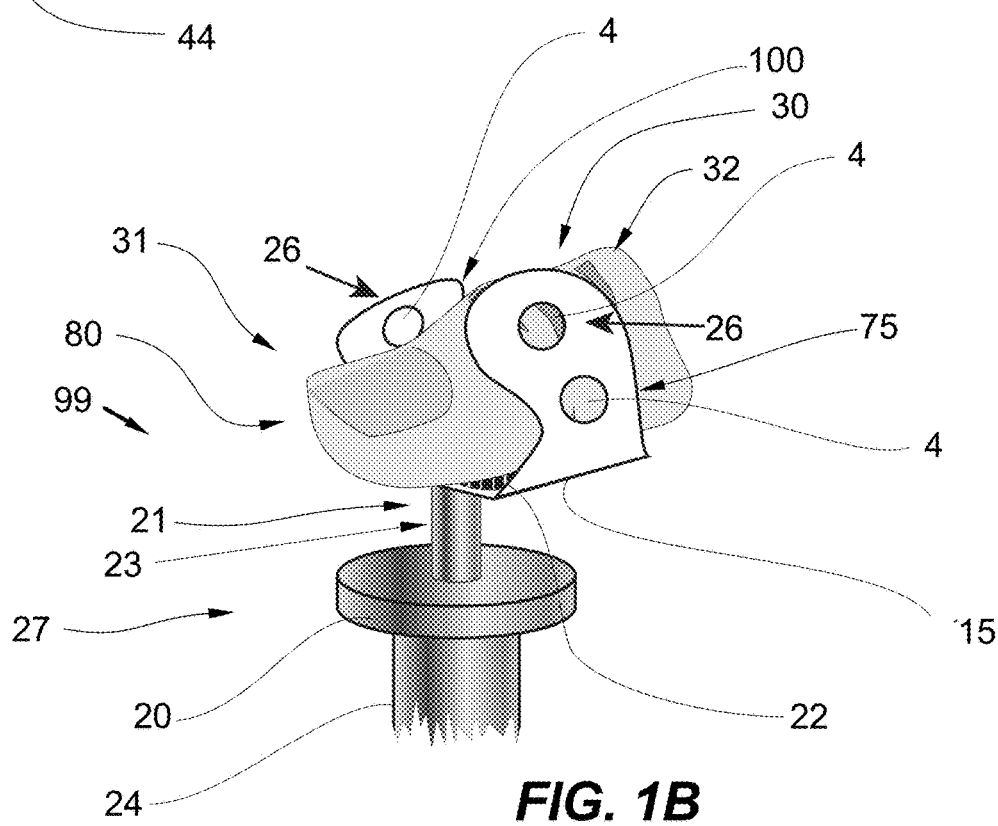

Many aspects of the disclosure can be better understood with reference to these figures. The elements and features shown in the figures are not necessarily to scale, emphasis being placed upon clearly illustrating the principles of example embodiments of the disclosure. Moreover, certain dimensions may be exaggerated to help visually convey such principles. In the figures, reference numerals often designate like or corresponding, but not necessarily identical, elements throughout the several views.

DETAILED DESCRIPTION OF EXAMPLE EMBODIMENTS

The technology will be discussed more fully hereinafter with reference to the Figures, which provide additional information regarding representative or illustrative embodiments of the disclosure. FIG. 1 provides, inter alia, disclosure relevant to using a ring in a representative application of performing a hypodermic injection. FIG. 2 provides, inter alia, disclosure relevant to a user representatively donning a ring. FIGS. 3, 4, 5, 6, 7, 8, 9, 10, 11, 12, 13, 14, 15, 16, 17, 18, 19, 20, 21, 22, 23, and 24 provide, inter alia, disclosure relevant to representative ring features. FIG. 24 provides, inter alia, disclosure relevant to methods or processes involving a ring.

The present technology can be embodied in many different forms and should not be construed as limited to the embodiments set forth herein; rather, these embodiments are provided so that this disclosure will be thorough and complete, and will fully convey the scope of the technology to those having ordinary skill in the art. Furthermore, all "examples," "embodiments," and "exemplary embodiments" provided herein are intended to be non-limiting, and among others supported by representations of the disclosure.

Those of ordinary skill in the art having benefit of this disclosure will be able, without undue experimentation, to combine compatible elements and features that are described in detail at various places in this written description, which includes text and illustrations. That is, the illustrations and specification are organized to facilitate practicing numerous combinations, such as combining an element of one illustrated embodiment with another element of another illustrated embodiment.

This document includes sentences, paragraphs, and passages (some of which might be viewed as lists) disclosing alternative components, elements, features, functionalities, usages, operations, steps, etc. for various embodiments of the disclosure. Unless clearly stated otherwise, all such lists, sentences, paragraphs, passages, and other text are not exhaustive, are not limiting, are provided in the context of describing representative examples and variations, and are among others supported by various embodiments of the disclosure. Accordingly, those of ordinary skill in the art having benefit of this disclosure will appreciate that the disclosure is not constrained by any such lists, examples, or alternatives. Moreover, the inclusion of lists, examples, embodiments, and the like (where provided) may help guide those of ordinary skill in practicing many more implementations and instances that embody the technology without undue experimentation, all of which are intended to be within the scope of the claims.

This disclosure includes figures and discussion in which features and elements of certain embodiments may be organized into what might be characterized as functional units, blocks, subsystems, or modules. And, certain processes and methods may be organized into blocks or into steps. Such organization is intended to enhance readership and to facilitate teaching the reader about working principles of the technology and about making and using an abundance of embodiments of the disclosure. The organization is not intended to force any rigid divisions or partitions that would limit the disclosure. In practice, the flexibility of the technology and the depth of this disclosure supports dispersing or grouping functionalities, elements, and features in many different ways. The inclusion of an element or function in one block, unit, module, or subsystem verses another may be substantially arbitrary in many instances, with the divisions being soft and readily redrawn using ordinary skill and this rich teaching. Accordingly, functional blocks, modules, subsystems, units, and the like can be combined, divided, repartitioned, redrawn, moved, reorganized, or otherwise altered without deviating from the scope and spirit of the disclosure. This is not to say that, nor will it support a conclusion that, any disclosed organizations and combinations are not novel, are not innovative, or are obvious.

The term "plunger," as used herein, generally refers to an elongate component that moves lengthwise in an elongate cavity, often in connection with moving matter into or out of the cavity. For example, a plunger may advance in a barrel of a hydraulic device to move matter out of the barrel or retract from the barrel to move matter out of the cylinder.

The term "fasten," as used herein, generally refers to physically coupling something to something else firmly or securely.

The term "fastener," as may be used herein, generally refers to an apparatus or system that fastens something to something else, whether releasably, temporarily, or permanently.

The term "couple," as may be used herein, generally refers to joining, connecting, or associating something with something else.

As one of ordinary skill in the art will appreciate, the term "operably coupled," as may be used herein, encompasses direct coupling and indirect coupling via another, intervening component, element, circuit, or module; moreover, a first component may be operably coupled to a second component when the first component comprises the second component.

The term "slot," as used herein, generally refers to an elongate aperture.

The term "palmar surface," as may be used herein with reference to a finger, a thumb, or a hand, generally refers to the surface of the finger, the thumb, or the hand located on the same side as the palm.

The term "friction ridge region," as may be used herein, generally refers to a region of the human anatomy that has friction ridges or epidermal ridges, such as the region of a thumb that leaves fingerprints.

As one of ordinary skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, process variations, and manufacturing tolerance.

Turning now to FIGS. 1A, 1B, 1C, and 1D, these figures illustrate an example ring 100 fastening an example plunger 21 to an example user 5 in an example medical application according to some embodiments of the disclosure. In the illustrated embodiment of FIG. 1, the plunger 21 is a component of a syringe 27, which in this example comprises a hypodermic syringe containing a material 43 to be injected. Thus, a system 99 comprising the ring 100, the syringe 27, and a material 43 is illustrated. As discussed in further detail below, in the illustrated example application, the ring 100 (among other capabilities) facilitates performing an aspiration to avoid inadvertent delivery of injected material 44 into a vascular lumen of a vein or artery (not illustrated).

In the illustrated embodiment, the syringe 27 comprises a barrel 24 and a finger flange 20, with the plunger 21 extending from the barrel 24 opposite a needle 25. The barrel 24 houses the material 43 to be injected. The example plunger 21 of the illustrated syringe 27 comprises a plunger head 19 that may have an elastomeric composition (for example synthetic rubber) for sealing the material 43 in the barrel 24. The plunger 21 further comprises a shaft 23 that extends out of the barrel 24 to a flange 22 that may comprise a thumb rest in some example embodiments. The flange 22 is disposed between a ring 100 and a thumb 30 of the user 5, with the shaft 23 extending through a slot 10 in the ring 100. In the example embodiment of FIG. 1, the ring 100 fastens the plunger 21 to the user's thumb 30. In some example embodiments, the ring 100 can be characterized as a fastener.

As illustrated, the example ring 100 comprises ends 26 that extend partially or fully about the thumb 30 and may extend past one another adjacent the user's thumbnail in some embodiments. In some example embodiments, the ends 26 extend at least half way around the thumb 30 and embrace the thumb 30. Thus, the ring 100 may fully or partially circumscribe the thumb 30, with 360 degrees of extension, less than 360 degrees of extension, or more than 360 degrees of extension.

As illustrated, the ends 26 comprise apertures 4, as will be discussed in further detail below. As illustrated, a distal portion 31 of the thumb 30 extends out of a distal opening 80 of the ring 100, and a proximal portion 32 of the thumb 30 extends out of a proximal opening 75 of the ring 100.

In operation, in the example illustrated in FIG. 1, the barrel 24 is disposed between the middle finger 29 and index finger 28 of the user 5, adjacent the finger flange 20 of the syringe 27. The user 5 can move his or her thumb 30 upward 34 along the axis 90 and away from the finger flange 20 and the index and middle fingers 28 and 29 to produce a retracting motion 36 of the plunger 21. Thus, a lower exterior surface 15 of the ring 100 and the plunger flange 22 (captured in the ring 100) move away from the finger flange 22. The index and middle fingers 28 and 29 can be situated above and below the finger flange 20 during retraction, for example. As discussed in further detail below with reference to FIG. 25, precision retraction and/or one-handed retraction of the plunger 21 can be useful for (among other things) performing an aspiration prior to injecting the material 43 in tissue 42 below the surface of the skin 41 at the injection site 40 of a patient 50. In some embodiments, the injection site 40 comprises a facial area of the patient 50, and FIG. 1 illustrates a facial filler injection. The patient 50 can comprise a human or a non-human animal or other appropriate subject. In some examples, a subject may be or comprise an inanimate object.

The user 5 can move his or her thumb downward 33 along the axis 90, towards the finger flange 20 and the index and middle fingers 28 and 29, to produce an advancing motion 35 of the plunger 21. Thus, the lower exterior surface 15 of the ring 100 and the plunger flange 22 move in unison towards the finger flange 20. Advancing the plunger 21 can cause delivery of the material 43 through a distal port 88 of the needle 44.

Figure 1C:
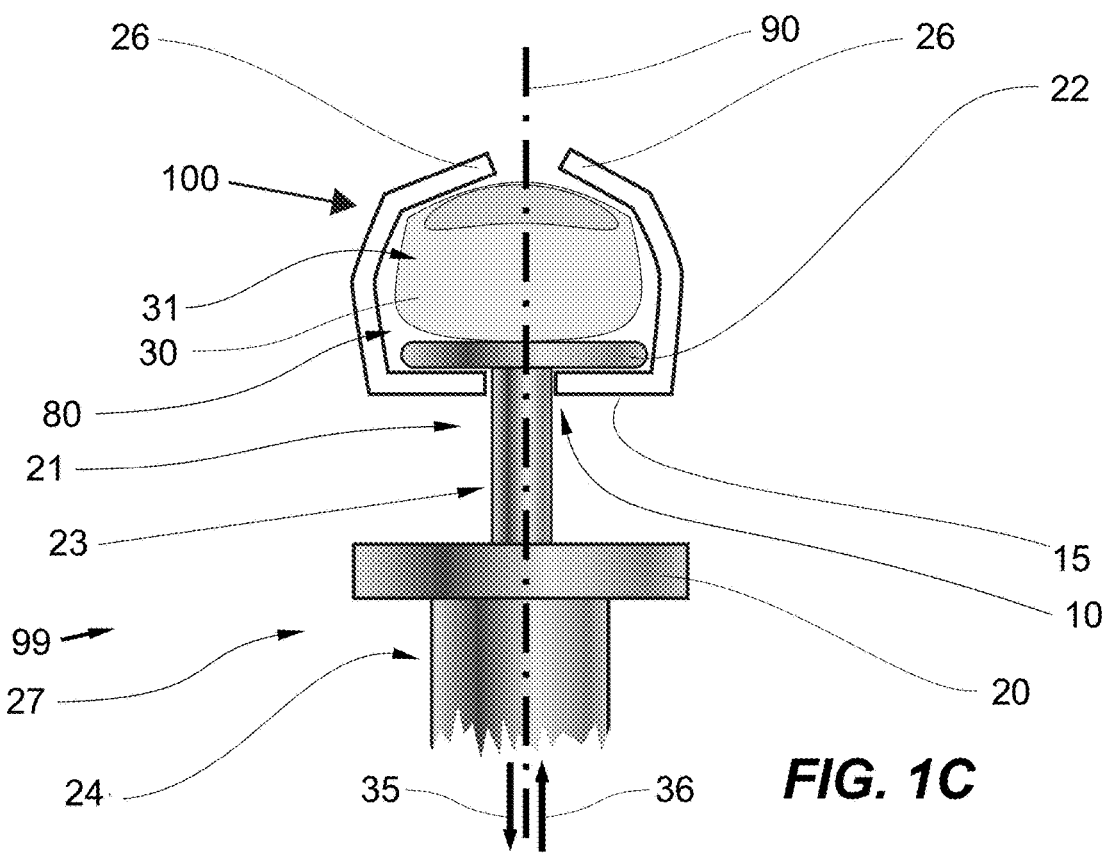
Figure 1D:
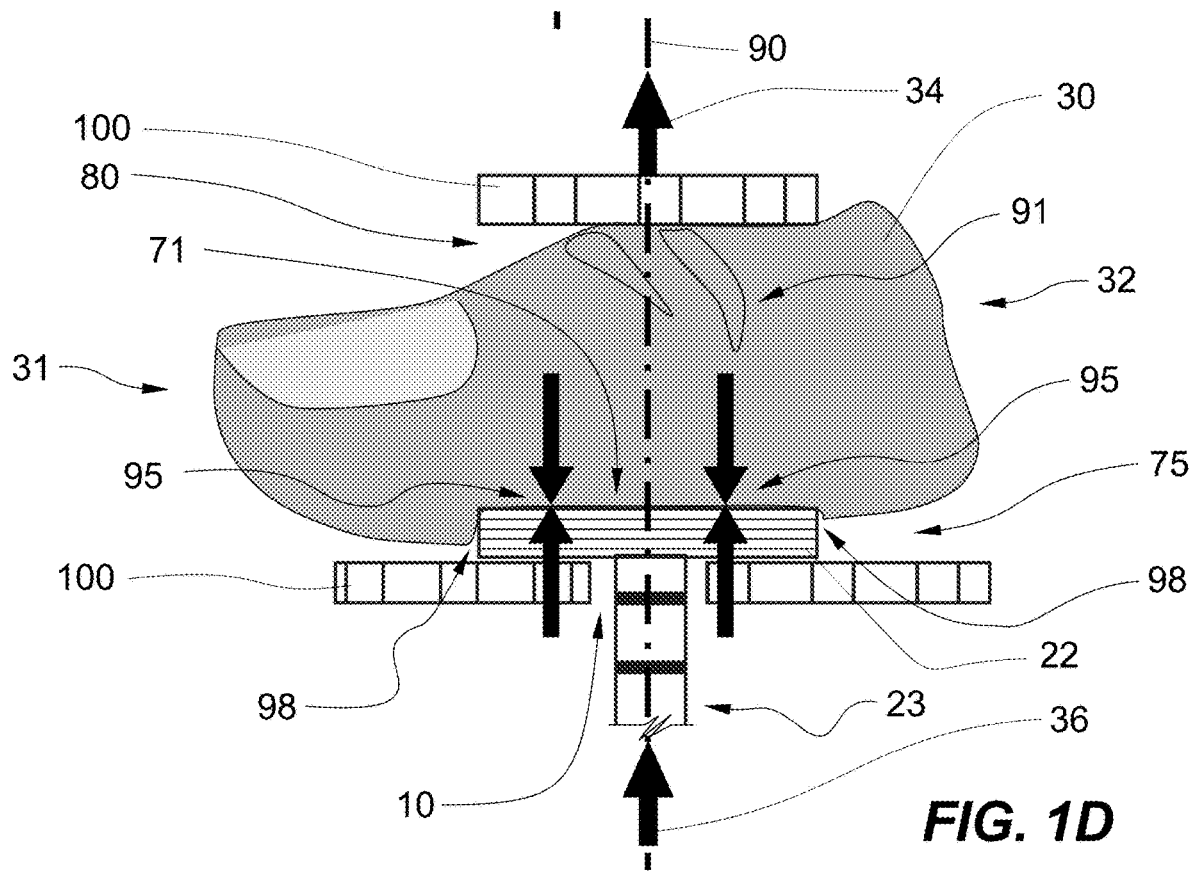

Referring now to FIG. 1D, the interphalangeal joint 91 of the user's thumb 30 (the most distal joint) can be positioned on the axis 90 in some example embodiments. (In some embodiments, the user 5 may prefer more distal or more proximal ring positioning than illustrated in FIG. 1D.) Throughout upward motion 34 of the user's thumb 30 and retraction 36 of the plunger 21, the plunger flange 22 and the thumb 30 can exert force 95 upon one another. As illustrated, the flange 22 can apply force 95 to the lower surface 71 of the thumb 30 during the entire time of a plunger retraction 36, and the force 95 can produce deformation of and a depression 98 in the lower surface 71 of the thumb 30. Thus, while the thumb 30 is lifting up, the flange 22 continues to exert force 95 on the lower surface 71 of the thumb 30 (and the lower surface 71 of the thumb 30 continues to exert force 95 on the flange 22.

Beyond assisting in retracting the plunger to avoid injecting in a vascular lumen, the ring 100 can be utilized to help position a distal port 88 of the needle 40 in a vascular lumen. For example, when drawing blood from a vascular lumen, injecting intravenously, or placing a catheter in a vascular lumen, the user 5 can retract the plunger 21 and look for aspirated blood as confirmation that the needle 40 is in the vascular lumen. Moreover, the ring 100 can increase dexterity of withdrawing fluids or aspiration in various medical and veterinary applications.

The user 5 can comprise a medical practitioner, for example a physician's assistant, a nurse, a physician, a technician, a nurse practitioner, a biomedical researcher, or other appropriate person. The user 5 can further comprise a person working in the veterinary field. In some embodiments, the user 5 can further comprise a person working in an industrial or nonmedical field.

The ring 100 can further heighten dexterity for retracting a plunger 21 or similar member using a biopsy device. Planes of injection (or of other intervention) can include subdermal, subcutaneous, intra muscular, intra vascular, peri osteo, and intraspinal forms, to mention some representative examples without limitation.

In some example embodiments, the material 43 comprises a dermal filler, such as the commercial dermal filler products marketed by Allergan under the registered trade names of "JUVEDERM," "VOLUMA," "VOLBNELLA," OR "VOLLURE;" by Galderma under the registered trade names of "RESTYLANE" AND "SCULPTRA; by Merz under the registered trade names of "RADIESSE, and BELOTERO; or by Suneva under the registered trade name of "BELLAFIL." In some example embodiments, the material comprises a dermal filler that comprises hyaluronic acid, calcium hydroxyapatite (CaHA) gel, poly-L-lactic acid fluid, injectable bovine collagen, or non-resorbable polymethylmethacrylate (PMMA) (not an exhaustive list).

Various other materials 43 to be injected may be housed in the barrel 24, such as medical agents intended for intramuscular delivery, for subcutaneous injection, or for intradermal injection, for example. Materials that may be delivered via intramuscular injection may include paliperidone, chlorpromazine, dimercaprol, ketamine, leuprorelin, naloxone, quinine, lorazepam, vaccines (e.g., rabies, hepatitis A, gardasil, influenza), fulvestrant, codeine, morphine, methotrexate, metoclopramide, olanzapine, streptomycin, diazepam, prednisone, antibiotics (e.g., penicillin), haloperidol, aripiprazole, interferon beta-1a, sex hormones, vitamin B12, risperidone, and platelet-rich plasma, to mention a few representative examples without limitation.

In some examples, a pharmaceutical company provides the syringe 27 prefilled with the material 43 to be injected. In other examples, the user 5 loads the material 43 into the syringe 27 at a point of care.

Turning now to FIGS. 2A and 2B, these figures illustrate example features of fastening a plunger 21 to a user 5 with a ring 100 according to some embodiments of the disclosure. FIG. 2A describes an example way of donning the ring 100. In the illustrated example, the plunger 21 is an element of a syringe 27 that comprises a barrel 24 and a finger flange 20 consistent with the foregoing discussion of FIG. 1.

As illustrated, the user 5 inserts the distal portion 31 of his or her thumb 30 into the proximal opening 75 of the ring 100 and inserts the shaft 23 of the plunger 21 into the slot 10 of the ring. Consequently, the flange 22 of the plunger 21 may be disposed between the user's thumb 30 and the floor 220 of the ring 100, with the shaft 23 of the plunger 21 extending through the slot 10, for example as illustrated at FIG. 1C. The distal portion 31 of the user's thumb 30 may extend out of the distal opening 80 of the ring, and the proximal portion 32 of the user's thumb 30 may extend out of the proximal opening 75 of the ring 100.

In some example embodiments, the user's thumb 30 is inserted into the proximal opening 75 and the plunger shaft 23 is inserted in the slot 10 so that the two insertions occur concurrently or during overlapping timeframes. In some example embodiments, the user 5 first inserts the plunger shaft 23 into the slot 10, and then the user 5 inserts his or her thumb 30 into the ring 100. In some example embodiments, the user 5 first inserts his or her thumb 30 into the ring 100, and then inserts the plunger shaft 23 into the slot 10. In some example embodiments, the user 5 inserts his or her thumb 30 partially into the ring 100, then inserts the plunger shaft 23 into the slot 10, and then pushes his or her thumb 30 further into the ring 100 until there is a tight fit.

As illustrated in FIG. 2B, a gap 230 can exist between the floor 220 of the ring 100 and the lower surface 71 of the thumb 30. In some example embodiments, the lower surface 71 of the thumb 30 can comprise a friction ridge region of the thumb 30 or a palmar surface of the thumb 30.

The plunger 21 can take up the gap 230 so that the user 5 can maintain pressure on the plunger flange 22 during retraction of the plunger 21, for example. Reducing or eliminating the gap 230 can reduce backlash or play during plunger operation in some example embodiments.

FIG. 2B further illustrates how the contours of the thumb 30 can follow or match the contours of the interior side surface 240 and the floor 220 of the ring 100. The like contours can promote a snug fit in some embodiments, for example.

In some example embodiments, apertures 4 can help avoid suction between the ring 100 and a medical glove (not illustrated) covering the thumb 30 while the user 5 is putting the ring 100 on or taking the ring 100 off. In some example embodiments, the apertures 4 can help hold the ring 100 on the user's thumb 30, as a result of increased friction at the peripheral edges of the apertures 4 or from the user's glove or thumb skin protruding slightly into the apertures 4. In some example embodiments, the apertures 4 support aesthetics and further may provide a receptacle for mounting a gem stone or other personalizing element.

Turning now to FIGS. 3A, 3B, 3C, and 3D, these figures illustrate an example ring 300 for fastening a plunger 21 to a user 5 according to some embodiments of the disclosure. The ring 300 illustrated in FIG. 3 represents an example embodiment of the ring 100 illustrated in FIGS. 1 and 2 and discussed above. The views of FIG. 3 illustrate example contours and features of an example embodiment in further detail as may be desirable in some applications, including from the perspectives of ergonomics and heightened precision and dexterity, for example. FIG. 3A illustrates a perspective view. FIG. 3B illustrates a side view FIG. 3C illustrates an end view. FIG. 3D illustrates a cross sectional view, with the cross section taken on the cut plane indicated in FIG. 3C.

The example ring 300 comprises a distal opening 80 with an associated distal edge 381 and a distal portion 380. A slot 10 extends into a floor 320 of the ring 300. The slot 10 comprises a mouth 305, a middle region 310, and a rear region 315. In the illustrated embodiment, the middle region 310 is narrower than the mouth 305 and is narrower than the rear region 315. As illustrated, the rear region 315 comprises one example of a curved outline at a closed end of a slot 10. The slot 10 comprise a rim in some embodiments.

Longitudinally opposite from the distal opening 80, the example ring 300 comprises a proximal opening 75 with an associated proximal edge 376 and a proximal portion 375. The ring ends 26 extend upward from a floor 320 of the ring 300 and form a section that extends longitudinally between the distal opening 80 and the proximal opening 75 of the ring 300. This section may partially or fully circumscribe an interior space 350 of the ring 300. Interior surfaces 340 of the ring 300 and the floor 320 define an interior space 350. The ends 26 comprise apertures 4, further discussed below.

As best seen in FIG. 3C, the floor 320 sags or curves downward to provide a recessed space 370 below corners 360. The recessed space 370 can have a depth 365 that accommodates at least a portion of a thickness of the flange 22 to promote plunger seating and retention by the ring 300, for example. In some example embodiments, the floor 320 further curves downward in the longitudinal dimension (orthonormal to the view of FIG. 3C). For example, a portion of the floor 320 that adjoins the rear region 315 of the slot 10 may be sunk below distal and proximal portions of the floor. A portion of floor 320 may provide an interior surface that is concave or that is shaped like a bowl or a saddle in some example embodiments.

Turning now to FIGS. 4A and 4B, these figures illustrate an example blank 400 to be formed into an example ring 300 for fastening a plunger 21 to a user 5 according to some embodiments of the disclosure. (See FIGS. 1 and 2, among other places, for example ring, plunger, and user illustrations.) FIG. 4A illustrates an overhead view (showing a major surface of the blank 400), while FIG. 4B illustrates a side view showing an edge thereof.

FIG. 4 provides reference numbers and lead lines indicating representative portions of the blank 400 corresponding to like-numbered features of the ring 300 illustrated in FIG. 3. When the blank 400 is formed, regions of the flat sheet of material can be transformed into three-dimensional contours of the ring 300 generally following the like numbers of FIGS. 3 and 4.

In some embodiments, the blank 400 comprises a thin sheet of workable metal alloy that is formed using metal working processes that create three-dimensional contours using permanent deformation. Representative metal working processes can include using tools and dies and/or bending over mandrels, among other techniques available to those of skill in the art having benefit of this disclosure. Specific portions can be heated and cooled in a manner that imparts desired softness or hardness to those regions, so that a user 5 may form a soft region for an individualized fit, for example.

In some example embodiments, the blank 400 comprises a sheet of thermoplastic material. Such a sheet can be transformed to provide the contours of the ring 300 of FIG. 3. For example, the sheet can be heated to soften the material and then formed using a tool and die or a mold or other appropriate process for working thermoplastics.

Turning now to FIG. 5, this figure illustrates an example ring 500 for fastening a plunger 21 to a user 5, depicted in the example configuration of disposed on a thumb 30 according to some embodiments of the disclosure. (See FIGS. 1 and 2 for example plunger illustrations.) The ring 500 can be utilized for fastening in accordance with the illustrations and associated discussion of FIGS. 1 and 2 and further with other teaching provided herein.

In some example embodiments, the ring 500 has a composition of a material that is sufficiently malleable so the user 5 can form the ring 500 by hand for an individualized fit to the user's thumb 30. As an example of forming the ring 500 by hand for an individualized fit, the user 5 may hold the ring 500 in the user's nondominant hand while bending the ring ends 26 with the user's dominant hand, without aid of a tool. In the context of describing malleability for forming by hand, such a user 5 may be a healthy male U.S. resident who is 35-45 years of age; is of average stature, body type, and weight; and has average strength. Of course, a wide range of users 5 of various ages, nationalities, residencies, genders, strengths, demographics, etc. may form various ring embodiments by hand.

In some example embodiments, the ring 500 has a metallic composition and may comprise one or more metals or metal alloys, may substantially consist of one or more metals or metal alloys, or may consist of one or more metals or metal alloys. In some embodiments, the ring 500 can comprise (or can consist or substantially consist of) a unitary piece of malleable metal, and the metal may comprise an alloy.

In some example embodiments, the ring 500 comprises a metal alloy and is supplied to the user 5 with the metal alloy annealed. In some example embodiments, as supplied to the user, a portion of the ring 500 is annealed. In some example embodiments, one or more selected portions of the ring 500 may be annealed to facilitate user forming of those ring portions. For example, the ring ends 26 may be annealed while the floor 320 of the ring 500 may be work hardened or otherwise hard relative to the annealed portion.

In some example embodiments, the material of the ring 500 can have a tensile strength, a yield strength, an elongation, or a hardness that has a numerical value that is within 25 percent of the corresponding numerical value of sterling silver. In some example embodiments, the material of the ring 500 can have a tensile strength, a yield strength, an elongation, or a hardness that has a numerical value that is within 10 percent of the corresponding numerical value of sterling silver. In some example embodiments, the material of the ring 500 can have a tensile strength, a yield strength, an elongation, or a hardness that is no greater than that of sterling silver. Some example embodiments may substantial deviate from the example values disclosed in this paragraph.

In some example embodiments, the ring 500 can have a material property, as annealed, that is in a range between 70 percent and 140 percent of any of the following values: tensile strength—207 MPa; yield strength—124 MPa; elongation—41%; tensile strength (wire)—283 MPa; elongation (wire)—40%; or hardness (wire)—71 HV. In some example embodiments, the ring 500 can have a material property, as half-hard, that is in a range between 70 percent and 140 percent of any of the following values: tensile strength (wire)—386 MPa; and hardness (wire)—95 HV. In some example embodiments, the ring 500 can have a material property, as full hard, that is in a range between 70 percent and 140 percent of any of the following values: tensile strength (wire)—496 MPa; and hardness (wire)—123 HV. In some example embodiments, the ring 500 can have a material property, as spring hard, that is in a range between 70 percent and 140 percent of any of the following values: tensile strength (wire)—552 MPa; and hardness (wire)—140 HV. The material properties disclosed in this paragraph (as with other materials and material properties disclosed at other portions of the detailed description) are examples; various embodiments may substantially deviate from these materials and properties, as may be deemed desirable for various applications and preferences.

FIG. 5 illustrates the ring 500 worn at an example location of a user's thumb 30. Various users 5 may have thumbs 30 of different sizes and shapes or may wear the ring at different locations on their thumbs 30 or on a finger other than a thumb 30 or on another appendage. A capability for user customization can help accommodate different user physiques, different user preferences, different plunger flanges 22, and different applications, for example.

In some example embodiments, the ring 500 is supplied to the user 5 with one or more mandrels, pliers, or other appropriate tools. The user 5 may utilize such tools to form the ring 500 to achieve a custom shape or personalized fit. In such embodiments, customization can be realized even if the user 5 cannot form the ring 500 barehandedly, for example when the ring 500 is too strong and/or the user 5 is not strong enough.

In some example embodiments, the user 5 may wear the ring 500 on a distal portion 31 the thumb 30, perhaps covering the fingernail (not shown in FIG. 5) where the thumb 30 is curved. The ring 500 may be formed (by the user 5 or by its manufacturer) with a corresponding curve in some example embodiments. In some example embodiments, the user 5 may wear the ring 500 over the interphalangeal joint 91 of the thumb 30, and the user 5 or the manufacturer may form the ring 500 to fit that anatomy. See FIG. 1D for an example illustration of the interphalangeal joint 91 disposed in the ring 500.

In some example embodiments, the user 5 may wear the ring 500 on a finger other than the thumb 30, or may wear the ring 500 on another appendage. The user 5 or the manufacturer may form the ring 500 to fit another finger or appendage, for example.

Turning now to FIGS. 6A and 6B, these figures illustrate an example ring 600 for fastening a plunger 21 to a user 5 according to some embodiments of the disclosure. (See FIG. 1 for example plunger and user illustrations.) The ring 600 can be utilized for fastening in accordance with the illustrations and associated discussion of FIGS. 1 and 2 and further with other teaching provided herein.

In the illustrated embodiment of FIG. 6, the proximal opening 75 of the ring 600 is larger than the distal opening 80 of the ring 600. As illustrated, the ring 600 tapers up longitudinally, between the distal edge 381 of the ring 600 and the proximal edge 378 of the ring 600. In the illustrated example embodiment, the slot 10 starts at the distal edge 381 of the ring 600 and extends towards the proximal edge 378. In some other example embodiments, the slot 10 starts at the proximal edge 378 of the ring 600 and extends towards the distal edge 381.

Turning now to FIG. 7, this figure illustrates an example ring 700 for fastening a plunger 21 to a user 5 according to some embodiments of the disclosure. (See FIG. 1 for example plunger and user illustrations.) The ring 1000 can be utilized for fastening in accordance with the illustrations and associated discussion of FIGS. 1 and 2 and further with other teaching provided herein.

In the example embodiment of FIG. 7, the floor 320 of the ring 700 is formed to promote retention and seating of the flange 5. As illustrated, the mouth 305 of the slot 10 in the floor 320 projects upward. More specifically two areas 710 that form the mouth 305 of the slot are bent into the interior space 350 of the ring 700. As illustrated, the bends largely occur at a crease line 720. These bends can be formed by positioning a corner or edge of a tool at the desired position and forming over the edge, resulting in the crease line 720. The bends can be more arching or more gradual based on the profile of the tool edge or by forming over a rod or other rounded surface. To facilitate such forming, the ring 700 can have a composition of malleable metal, for example annealed metal, gold, sterling silver, Argentium silver, copper, or other appropriate metal or metal alloy. In some embodiments, the ring 600 comprises stainless steel. In some examples, the illustrated contours and features are formed by injection molding a thermoplastic material.

FIG. 7 illustrates the ring 700 with the slot mouth 305 at the distal portion of the ring 700. In some other example embodiments, the slot mouth 305 is at the proximal portion of the ring 700.

Turning now to FIGS. 8A and 8B, these figures illustrate an example ring 800 for fastening a plunger 21 to a user 5 according to some embodiments of the disclosure. (See FIG. 1 for example plunger and user illustrations.) FIG. 8B provides a magnified view of a portion 811 of the ring 800 that is outlined in FIG. 8A. The ring 800 can be utilized for fastening in accordance with the illustrations and associated discussion of FIGS. 1 and 2 and further with other teaching provided herein.

As best seen in the magnified view of FIG. 8B, the ring 800 comprises a distally oriented curled edge 820 adjacent the slot 10. The curled edge 820 can help secure the plunger flange 20 against the floor 320. The slot 10 comprises a pair of nubs 810 that promote retention of the plunger shaft 23 in the slot 10.

In the example ring 800, the ends 26 are oriented upright relative to the floor 320. In some embodiments, the ring 800 is supplied in this configuration in malleable metal, and the user 5 bends the ring 800 as desired for a custom fit.

Turning now to FIG. 9, this figure illustrates an example ring 900 for fastening a plunger 21 to a user 5 according to some embodiments of the disclosure. As illustrated, the ring 900 is positioned to show the lower exterior surface 15, including a curled edge 820 that is similar in form and function to the curled edge 820 illustrated in FIG. 8 and discussed above. The slot 10 in the ring 900 is rounded and wide at its closed end relative to the slot 10 of the ring 800 of FIG. 8.

Figure 10A:
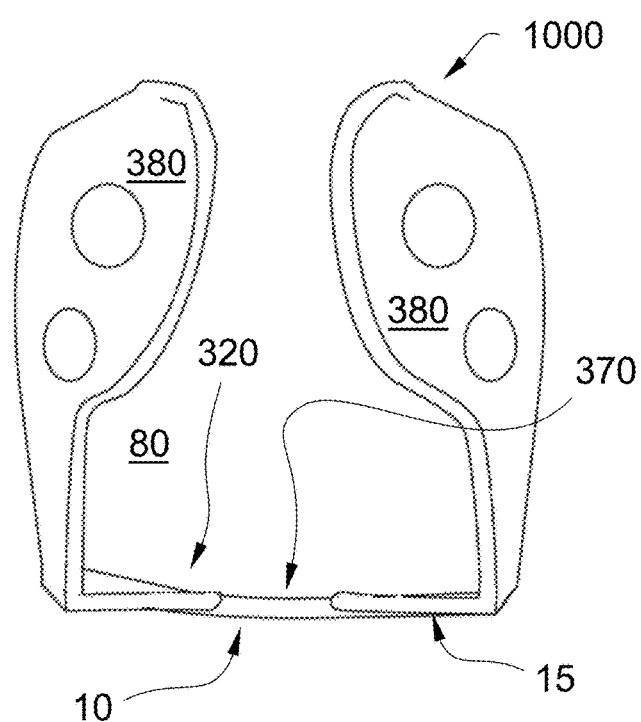
FIGS. 10A and 10B, collectively
Figure 10B:
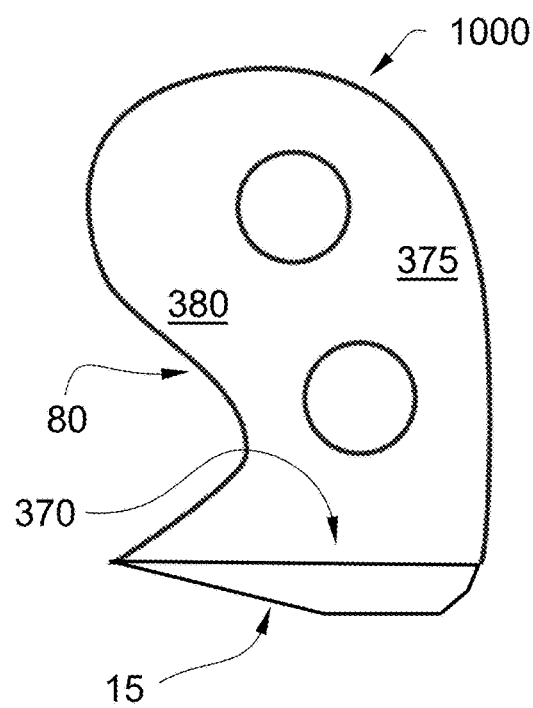

Turning now to FIGS. 10A and 10B, these figures illustrate an example ring 1000 for fastening a plunger 21 to a user 5 according to some embodiments of the disclosure. (See FIG. 1 for example plunger and user illustrations.) The ring 1000 can be utilized for fastening in accordance with the illustrations and associated discussion of FIGS. 1 and 2 and further with other teaching provided herein. FIG. 10A illustrates the ring 1000 with the distal opening 80 and the distal portions of the ring 1000 facing out of the page. Meanwhile, FIG. 10B illustrates the ring 1000 with those features oriented left and the proximal portions of the ring 1000 oriented right.

As best seen in FIG. 10B, the floor 320 of the ring 1000, and thus the lower exterior surface 15 of the ring 1000, bulges downward. This provides a recessed space 370 that is inside the ring 1000 associated with the slot 10 for receiving flanges 22 of different geometries that different manufacturers produce.

Figure 11:
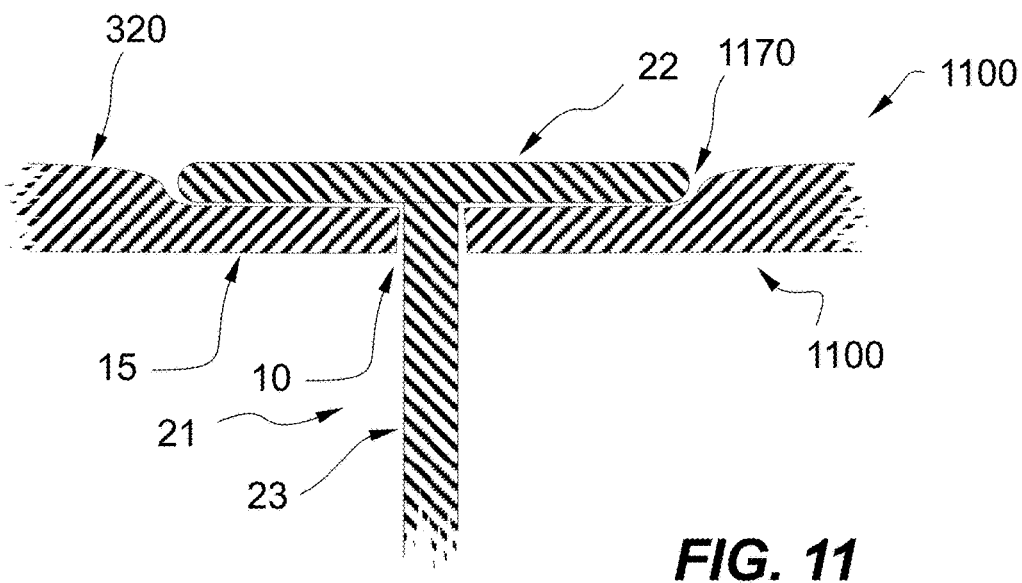
FIG. 11 is an illustration of a portion of a ring for fastening a plunger to a user in accordance with some example embodiments of the disclosure.

Turning now to FIG. 11, this figure illustrates a portion of an example ring 1100 for fastening a plunger 21 to a user 5 (not depicted in FIG. 11) according to some embodiments of the disclosure. More specifically, FIG. 11 illustrates a cross section of the ring 1100 and the plunger 21, with the plunger's shaft 23 extending through the slot 10 in the floor 320 of the ring 1100.

In the example embodiment of FIG. 11, the floor 320 comprises a recessed area 1170 in which the flange 22 of the plunger 21 is disposed and is seated. As illustrated, the recessed area 1170 is sized to receive the flange 22. In some example embodiments, the recessed area 1170 is configured to receive a wide range of flange sizes and geometries as produced from different manufacturers. In some other example embodiments, the recessed area 1170 has a geometry designed for selective compatibility with a particular manufacturer's flanges. For example, the shape and/or dimensions of the recessed area 1170 may receive proprietary flanges of one manufacturer that have a corresponding size and/or dimensions (or other matching physical features) without fully accommodating other flanges from other manufacturers.

Figure 12:
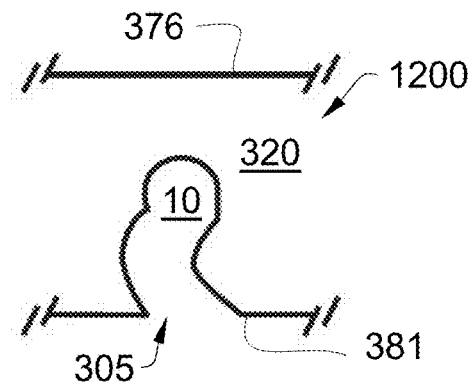
FIG. 12 is an illustration of a portion of a ring for fastening a plunger to a user in accordance with some example embodiments of the disclosure.

Turning now to FIG. 12, this figure illustrates a portion of an example ring 1200 for fastening a plunger 21 to a user 5 according to some embodiments of the disclosure. (See FIG. 1 for example plunger and user illustrations.) FIG. 12 illustrates a floor 320 of the ring 1200 with an example slot 10 that is curved along its length. The illustrated portion of the ring 1200 can be utilized for fastening in accordance with the illustrations and associated discussion of FIGS. 1 and 2 and further with other teaching provided herein.

As illustrated at FIG. 12, the slot 10 has a mouth 305 at the distal edge 381 and extends from the distal edge 381 towards the proximal edge 376. In some other embodiments, the mouth 305 is at the proximal edge 376, and the slot 10 extends from the mouth 305 towards the distal edge 381. In various embodiments, the floor 320 can have a metallic or plastic composition, and/or comprise multiple components of different materials joined together.

In this illustrated example, the slot 10 deviates from linear along a path from the mouth at distal edge 381 towards proximal edge 376. The deviation from linear can help secure or retain the plunger 21 in the slot 10, for example. In various embodiments, the path of the slot 10 may be sinusoidal, sinuous, serpentine, arced, bent, or another appropriate form of a curve. In some example embodiments, the path is of the slot 10 includes one or more corners, a sharp bend, or may turn back on itself. For example, the path may have shape of the letter "J." In such an embodiment, the top of the "J" may be at the distal edge 381 and the curved bottom of the letter "J" may be oriented towards the proximal edge 376. In various example embodiments, the slot 10 follows another appropriate path operable to fasten the plunger 21 to the user 5.

Figure 13:
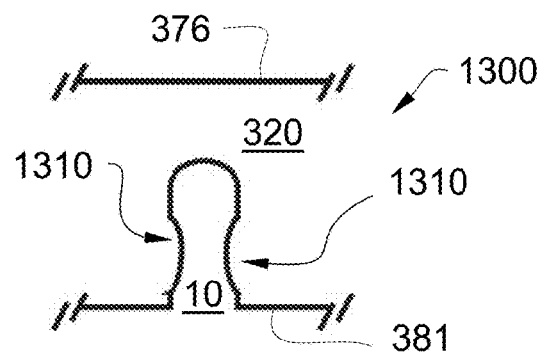
FIG. 13 is an illustration of a portion of a ring for fastening a plunger to a user in accordance with some example embodiments of the disclosure.

Turning now to FIG. 13, this figure illustrates a portion of an example ring 1300 for fastening a plunger 21 to a user 5 according to some embodiments of the disclosure. (See FIG. 1 for example plunger and user illustrations.) FIG. 13 corresponds to FIG. 12, as discussed above. The illustration portion of the ring 1300 can be utilized for fastening in accordance with the illustrations and associated discussion of FIGS. 1 and 2 and further with other teaching provided herein.

As illustrated by FIG. 13, the slot 10 starts at the distal edge 381 and extends from the distal edge 381 towards the proximal edge 376. In some other embodiments, the slot 10 is open at the proximal edge 376 and extends towards the distal edge 381.

In the example embodiment of FIG. 13, the slot 10 has sidewall regions 1310 that bow inward to help secure or retain the plunger 21 in the slot 10. In some embodiments, the bow sufficiently narrows the slot 10 so that interference exists between the outer diameter of the plunger shaft 23 and the slot 10. Thus, at least some material deformation can occur upon insertion of the plunger 21 into the slot 10, thereby aiding plunger retention.

Figure 14:
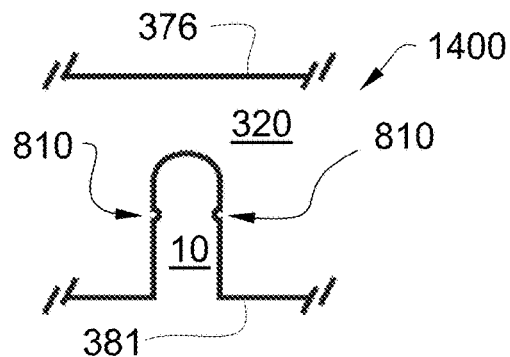
FIG. 14 is an illustration of a portion of a ring for fastening a plunger to a user in accordance with some example embodiments of the disclosure.

Turning now to FIG. 14, this figure illustrates a portion of an example ring 1400 for fastening a plunger 21 to a user 5 according to some embodiments of the disclosure. (See FIG. 1 for example plunger and user illustrations.) FIG. 14 corresponds to FIGS. 12 and 13, as discussed above. The illustration portion of the ring 1400 can be utilized for fastening in accordance with the illustrations and associated discussion of FIGS. 1 and 2 and further with other teaching provided herein.

As illustrated in FIG. 14, the slot 10 starts at the distal edge 381 and extends from the distal edge 381 towards the proximal edge 376. In some other embodiments, the slot 10 is open at the proximal edge 376 and extends towards the distal edge 381.

In the example embodiment of FIG. 14, the slot 10 has nubs 810 that narrow the slot 10 to help secure or retain the plunger 21 in the slot 10. In some example embodiments, the nubs 810 can comprise sharp or pointed perturbances. In some example embodiments, the nubs 810 are formed of different material than the rest of the floor 320. For example, the floor 320 can be formed of plastic material and nubs made of metal inserted into the plastic material during injection molding or other appropriate fabricating operation. The illustrated example embodiment of FIG. 14 can comprise a composite structure or a can be formed of homogenous material.

Figure 15:
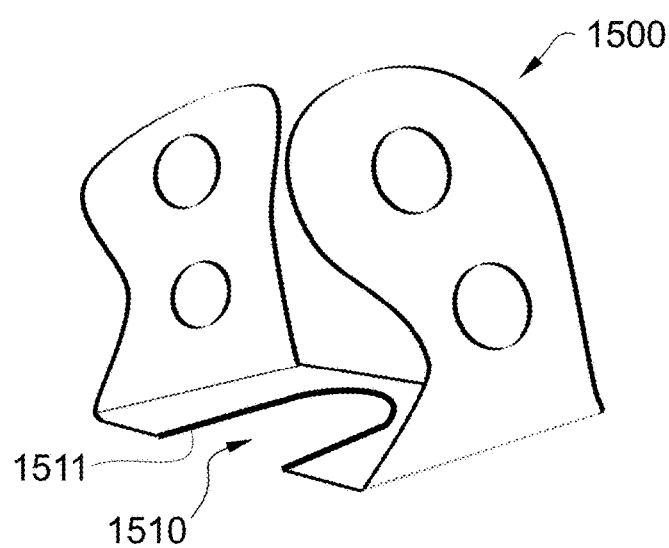
FIG. 15 is an illustration of a ring for fastening a plunger to a user in accordance with some example embodiments of the disclosure.
Figure 16:
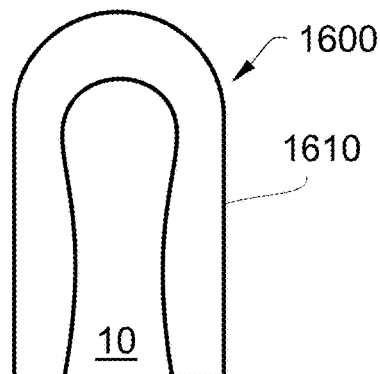
FIG. 16 is an illustration of a portion of a ring for fastening a plunger to a user in accordance with some example embodiments of the disclosure.
Figure 17:
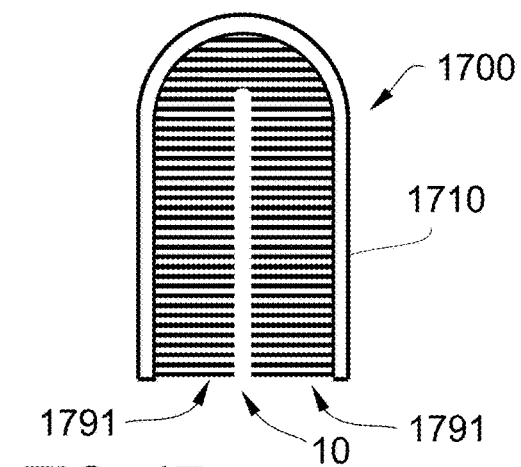
FIG. 17 is an illustration of a portion of a ring for fastening a plunger to a user in accordance with some example embodiments of the disclosure.

Turning now to FIGS. 15, 16, and 17, these figures will be discussed. FIG. 15 illustrates an example ring 1500 for fastening a plunger 21 to a user 5 according to some embodiments of the disclosure. FIGS. 16 and 17 illustrate respective portions of an example ring 1500 for fastening a plunger 21 to a user 5 according to some embodiments of the disclosure. (See FIG. 1 for example plunger and user illustrations.) As further discussed below, FIGS. 16 and 17 respectively illustrate inserts 1600, 1700 that mate with receptacle 1510 of the ring 1500 illustrated in FIG. 15. In combination with one of the inserts 1600, 1700, the ring 1500 can be utilized for fastening in accordance with the illustrations and associated discussion of FIGS. 1 and 2 and further with other teaching provided herein.

The insert 1600 illustrated in FIG. 16 is sized for insertion in and reception by the receptacle 1510 of the ring 1500, to become a component of the ring 1500. The insert 1600 comprises a slot 10 that may be configured in accordance with the various slot embodiments disclosed herein.

In some example embodiments, the insert 1600 is configured for compatibility with a particular type or brand of syringe 27. In some example embodiments, the insert 1600 can be optimized for a specific manufacturer's syringes or may be configured to work only with a proprietary plunger. A syringe manufacturer may supply the insert 1600 so the user 5 can change out the insert 1600 as needed, for example on a procedure-by-procedure basis or otherwise as desired.

In some example embodiments, the insert 1600 can be snapped into the receptacle 1510 by the user 5, for example. In some embodiments, the ring 1500 is formed of a material that is harder than the insert 1600 to facilitate user assembly. For example, the insert 1600 can be made of plastic or synthetic rubber, and the ring 1500 can be made of metal. As another example, the ring 1500 and the insert 1600 can both be made of plastic materials having different durometers, with the ring 1500 having a higher durometer than the insert or vice versa.

In some embodiments, the insert 1600 can comprise a groove (not illustrated) that extends about the outer periphery 1610 of the insert 1600. Such a groove can receive the edges 1511 of the ring 1500 that form the receptacle 1510. Thus, the insert 160 can snap into the receptacle 1510 in a tongue-in-groove configuration, with the insert 1600 comprising the groove and the receptacle edge 1511 comprising the tongue.

As illustrated, the receptacle 1510 comprises a slot with substantially parallel sides. In some embodiments, the edges 1511 of the receptacle 1510 can be curved to promote retention of the insert 1600. For example, the receptacle 1510 can have a width that increases with depth, and the insert 1600 can have a corresponding geometry.

In some example embodiments, the insert 1600 is permanently joined with the receptacle 1510 during manufacture of the ring 1500. For example, the insert 1600 can be fused, epoxied, welded, bonded, or otherwise attached to the ring 1500.

The receptacle 1510 of the ring 1500 can receive the insert 1700 illustrated in FIG. 17 in keeping with the foregoing discussion of the insert 1600. In some example embodiments, the insert 1700 comprises a pliable material 1791 that extends inward from the outer periphery of the insert 1700. The pliable material 1791 can comprise a thin sheet of elastomeric material, such as silicone or synthetic rubber, with the slot 10 formed in the sheet, for example.

In some embodiments, the pliable material 1791 comprises thin filaments, for example bristles, whiskers, or fibers, that extend inward from the periphery 1710 of the insert 1700 towards the slot 10. The slot 10 can thus be formed by the ends of such filaments, which can comprise natural or synthetic fibers, for example as may be incorporated in a typical hairbrush.

Figure 22:
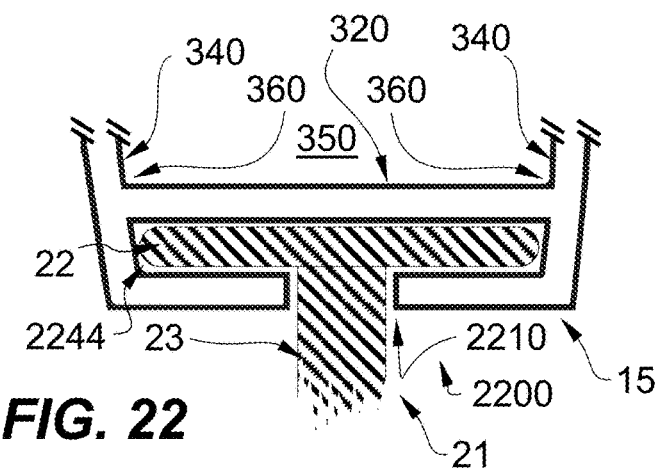
FIG. 22 is an illustration of a portion of a ring for fastening a plunger to a user in accordance with some example embodiments of the disclosure.

In some embodiments, such filaments are attached directly to the ring 1500, without use of an insert. In some embodiments, such filaments form an aperture other than a slot, for example a circle, rectangle, or other closed geometric form in a floor 320 of a ring. FIG. 22, as further discussed below, illustrates an example embodiment of a geometric form.

Turning now to FIGS. 18A and 18B, these figures illustrate an example ring 1800 for fastening a plunger 21 to a user 5 according to some embodiments of the disclosure. (See FIG. 1 for example plunger and user illustrations.) The ring 1800 can be utilized for fastening in accordance with the illustrations and associated discussion of FIGS. 1 and 2 and further with other teaching provided herein.

The example ring 1800 illustrated in these FIGS. 18A and 18B comprises flexible material and straps on with a catch 1864 that can provide a snug or secure fit. In the illustrated embodiment, the ring 1800 can be characterized as comprising a strap that can be tightened.

As illustrated by FIG. 18A, the ends 26A, 26B of the ring 1800 are depicted in a free state. In the illustration of FIG. 18B, the catch 1864 has the ends 26A, 26B connected to one another.

In the illustrated example, the catch 1864 comprises an array of protrusions 1866 disposed on the end 26B and an aperture 1844 in the end 26A. The aperture 1844 is sized to receive the end 26B. As illustrated, the protrusions 1866 are curved to engage the periphery of the aperture 1844 once the end 26B is sufficiently inserted in the aperture 1844. In some other example embodiments, the catch 1864 can comprise a buckle, clasp, clamp, clip, hasp, or other appropriate device.

FIG. 18B illustrates the ring 1800 as may be disposed on a user's thumb 30 prior to tightening. Once on the thumb 30 in the configuration illustrated in FIG. 18B, the user 5 can tighten the ring 1800 by pulling on the free end 26B, for example upward or in a direction so the end 26B turns somewhat back on its self. The slot 10 provides for fastening the plunger 21 to the user 5 as discussed above with reference to FIGS. 1 and 2.

In some example embodiments, the ring 1800 can comprise a flexible synthetic material or a combination of such materials, such as nylon, acetal resin, silicone, vinyl, flashspun high-density polyethylene fibers, one or more elastomers, or other appropriate material. In some example embodiments, the ring 1800 can comprise nonwoven fabric.

In some example embodiments, the ring 1800 comprises a homogenous thermoplastic, for example nylon. In some embodiments, the floor 320 is thick relative to the end 26A and the end 26B. Thickening the floor 320 can enhance stiffness of this area of the ring 1800.

In the illustrated embodiment, the ring 1800 comprises corners 360 adjacent the floor 320. The corners 360 can result from manufacturing the ring 1800 with pre-defined corners, so the corners 360 exist with the ring 1800 is in a relaxed state or prior to strapping on the ring 1800. For example, the ring 1800 can be injection molded from thermoplastic material in a mold having a corresponding corner. As another alternative, the corners 360 may be formed in a flat strip of thermoplastic by heating the strip at a location where the corner 360 is desired to soften the material, bending the strip at that location, and then cooling the material.

Turning now to FIG. 19, this figure illustrates an example ring 1900 for fastening a plunger 21 to a user 5 according to some embodiments of the disclosure. (See FIG. 1 for example plunger and user illustrations.) The ring 1900 can be utilized for fastening in accordance with the illustrations and associated discussion of FIGS. 1 and 2 and further with other teaching provided herein.

Similar to the embodiment illustrated in FIG. 18 and discussed above, the example ring 1900 is configured for strapping to a thumb 30 of the user 5 by inserting the end 26B in the aperture 1844 of the end 26A and tightening.

In the example embodiment illustrated in FIG. 19, the aperture 1944 comprises a slit that may formed be formed in the end 26A by cutting without material removal. Relative to the embodiment illustrated by FIG. 18, the protrusions 1966 on the end 26B are smaller and more numerous, which may support a fine level of control of tightening as may be appropriate in some environments or applications.

For the embodiment of FIG. 19, the ring 1900 can be formed from a thin strip of material. In some examples, the material comprises a thermoplastic such discussed above with reference to the ring 1800 illustrated by FIG. 18. To facilitate formation of corners 360 (see FIG. 18) adjacent the floor 320 when worn by the user 5, features 1960 can be formed in strip of material. For example, the features can be formed in the strip with scribing, perforations, notching, deformations, thinning, stress deformation, heating, creasing, or other appropriate means.

Turning now to FIG. 20, this figure illustrates an example portion of a ring 200 for fastening a plunger 21 to a user 5 according to some embodiments of the disclosure. (See FIG. 1 for example plunger and user illustrations.) The illustrated portion of the ring 2000 can be utilized for fastening in accordance with the illustrations and associated discussion of FIGS. 1 and 2 and further with other teaching provided herein.

FIG. 20 illustrates a floor 320 of the ring 2000 and portions of the interior surface 340 of the ring 2000. In the illustrated example of FIG. 20, the ring 2000 comprises features 1960 associated with a corner, crease, or sharp bend, for example as discussed above with reference to FIG. 19.

An aperture 2010 is formed in or disposed adjacent the floor 320 and is disposed between a distal portion 380 and a proximal portion 375 of the ring 2000. The aperture 2010 is configured for receiving and securing a flange 22 of a plunger 21. As illustrated, the example aperture 2010 comprises two slit areas 2001 that oppose one another, each extending towards a respective one of the features 1960. The illustrated aperture 2010 comprises one example embodiment of a slot.

In an example embodiment, the floor 320 comprises an elastomeric sheet of material, and the aperture 2010 is formed in that material. In operation, the user 5 can use the slit areas 2001 of the aperture 2010 to work the flange 22 into the aperture 2010. The distance between the opposing ends of the slit areas 2001 can correspond to the width of the flange 22, so that the aperture 2010 can receive the flange 22. For example, the distance between the opposing ends of the slit area 2001 can be less than the width of the flange 22, so that the user may stretch the elastomeric material to open the aperture 2010 for insertion of the flange 22.

In some example embodiments, the flange 22 is rectangular, oblong, or oval. In some such embodiments, the user may use the narrow dimension of the flange 22 to work the flange 22 into the aperture 2010. Once in, the user 22 may rotate the flange 90 degrees so the flange 20 is held securely behind the floor 320.

In some example embodiments, the user's thumb 30 (or a medical glove) directly contacts at least a portion of the elastomeric sheet of the floor 320. In such embodiments, the flange 22 may likewise contact the user's thumb 30 when the flange 22 is inserted in the aperture and the ring 2000 is on the user's thumb 30. Alternatively, a portion of the ring 2000 may be disposed between the user's thumb 30 and the flange 22. For example, the ring 1900 illustrated in FIG. 19 or the ring 300 illustrated in FIG. 3 can be formed without the illustrated slot 10, so the floor 320 of the ring 1900 or the ring 300 is unbroken. An elastomeric sheet comprising the aperture 2010 can be attached to the ring 1900 or the ring 300 so that the sheet forms a lower exterior surface of the ring 1900 or 300 (in the location indicated by reference number 15 on FIG. 3).

Turning now to FIG. 21, this figure illustrates an example portion of a ring for fastening a plunger 21 to a user 5 according to some embodiments of the disclosure. (See FIG. 1 for example plunger and user illustrations.) The illustrated portion of the ring 2100 can be utilized for fastening in accordance with the illustrations and associated discussion of FIGS. 1 and 2 and further with other teaching provided herein. In some example embodiments, features of the ring 2100 illustrated in FIG. 21 can be implemented and practiced in keeping with the foregoing discussion of FIG. 20.

As illustrated, the aperture 2110 of the ring 2100 comprises a single slit area 2101 that is oriented towards the distal portion 380 of the ring 2100, generally parallel to the features 1960. In some other example embodiments, the slit area 2101 is oriented towards the proximal portion 375 of the ring 2100. In some example embodiments, the slit area 2101 is oriented towards either of the features 1960 or at an angle in between them.

Turning now to FIG. 22, this figure illustrates an example portion of a ring 2200 for fastening a plunger 21 to a user 5 according to some embodiments of the disclosure. (See FIG. 1 for an example user illustration.) The illustrated portion of the ring 2200 can be utilized for fastening in accordance with the illustrations and associated discussion of FIGS. 1 and 2 and further with other teaching provided herein.

FIG. 22 illustrates an example embodiment in which a floor 320 of the ring 2200 separates the flange 22 from the user's thumb 30, which is a configuration discussed above with reference to FIG. 20. The ring 2200 comprises a cavity 2244, in which the flange 22 is disposed, and a slot 2210 through which the shaft 23 extends. A lower exterior surface 15 of the ring 2200 extends below the cavity 2244. The ring 2200 further comprises corners 360 and interior surfaces 340 that extend about an interior space 350 in which the user's thumb 30 is disposed when the ring 2200 is worn.

Figure 23A:
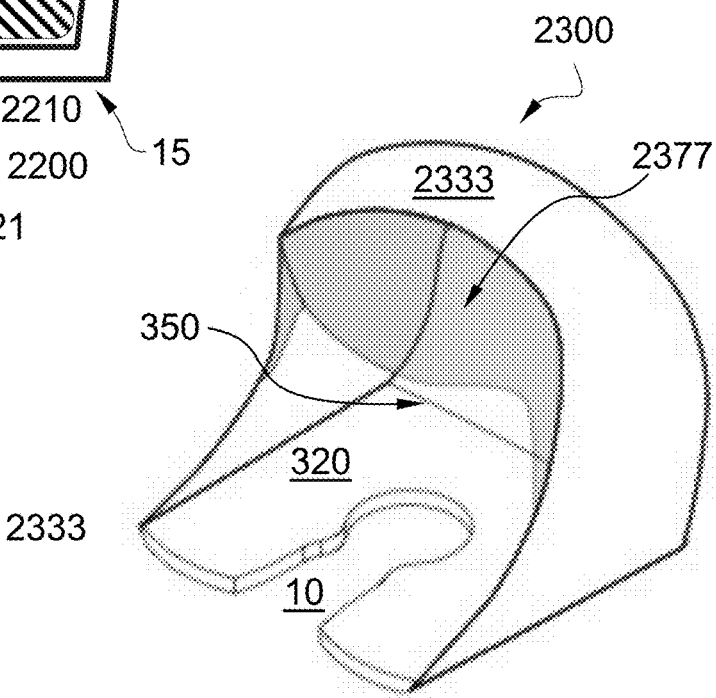
FIGS. 23A and 23B, collectively
Figure 23B:
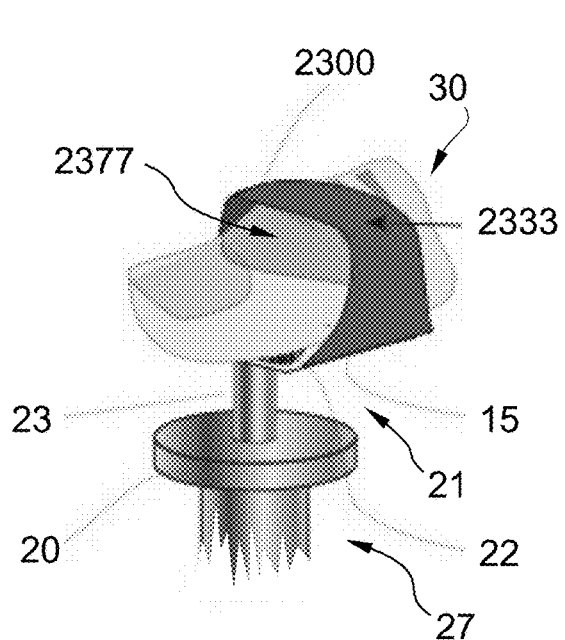
Figure 24:
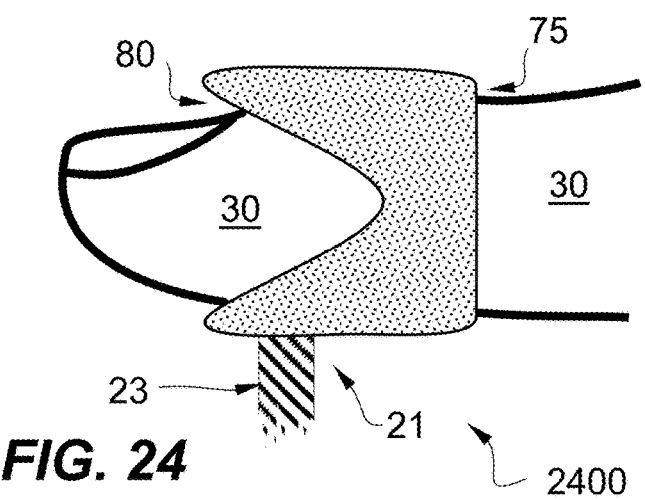
FIG. 24 is an illustration of a ring for fastening a plunger to a user in accordance with some example embodiments of the disclosure.

Turning now to FIGS. 23A and 23B, these figures illustrate an example ring 2300 for fastening a plunger 21 to a user 5 according to some embodiments of the disclosure. As illustrated in FIG. 23B, the example ring 2300 extends continuously and fully around the user's thumb 30 when worn. A plastic material 2377 extends across an upper region of the interior space 350 of the ring 2300 and is attached to the upper portion 2333 of the ring 2300. The plastic material 2377 extends from the upper portion 2333 of the ring 2300 towards the floor 320, the slot 10, and the lower exterior surface 15 of the ring 2300. In operation, as shown in FIG. 23B, the plastic material 2377 deforms and presses on the thumb 30 to ensure a snug fit. In some example embodiments, the plastic material 2300 comprises a thin sheet of thermoplastic or silicone. In some example embodiments, the plastic material 2300 comprises a bladder or balloon. In some example embodiments, the entire ring 2300 can have a plastic composition that comprises one or more appropriate materials disclosed herein or otherwise available in the art.

Turning now to FIG. 24, this figure illustrates an example ring 2400 for fastening a plunger 21 to a user 5 according to some embodiments of the disclosure. In the illustrated example embodiment, the ring 2400 fully circumscribes the thumb 30 on which the ring 2400 is worn.

As illustrated, the ring 2400 comprises a slot (hidden in the view of FIG. 24) in accordance with the slot 10 illustrated in FIG. 23A or another appropriate slot supported by the present disclosure. The ring 2400 fastens the plunger 21 to the thumb 30 of the user 5, with the shaft 23 of the plunger 21 protruding through the slot 10, and with the flange 22 (hidden in the view of FIG. 24) disposed between the ring 2400 and the thumb 30.

The thumb 30 extends from the proximal aperture 75 of the ring 2400 to the distal opening 80 and protrudes out of the distal opening 80. As illustrated, the interphalangeal joint 91 of the thumb 30 (illustrated at FIG. 1D) is disposed inside the ring 2400 and is hidden in the present view. In operation, a user 5 can flex this joint 91 during retraction of the plunger 21. Flexing the interphalangeal joint 91 can press the lower surface 71 of the thumb 30 against the flange 22 while pressing the upper surface of the interphalangeal joint 91 against the upper interior surface of the ring 2400. Thus, gap is taken up and pressure is maintained against the flange 22 during retraction of the plunger 21. In some embodiments, hyperextension of the joint 91 can take up gap and similarly provide ongoing force against the plunger flange 22 during plunger retraction.

In some example embodiments, the ring 2400 is formed of a thermoplastic material such as nylon or acetal resin. In some example embodiments, the ring 2400 may be formed of metal or other appropriate material supported by the present disclosure.

Figure 25:
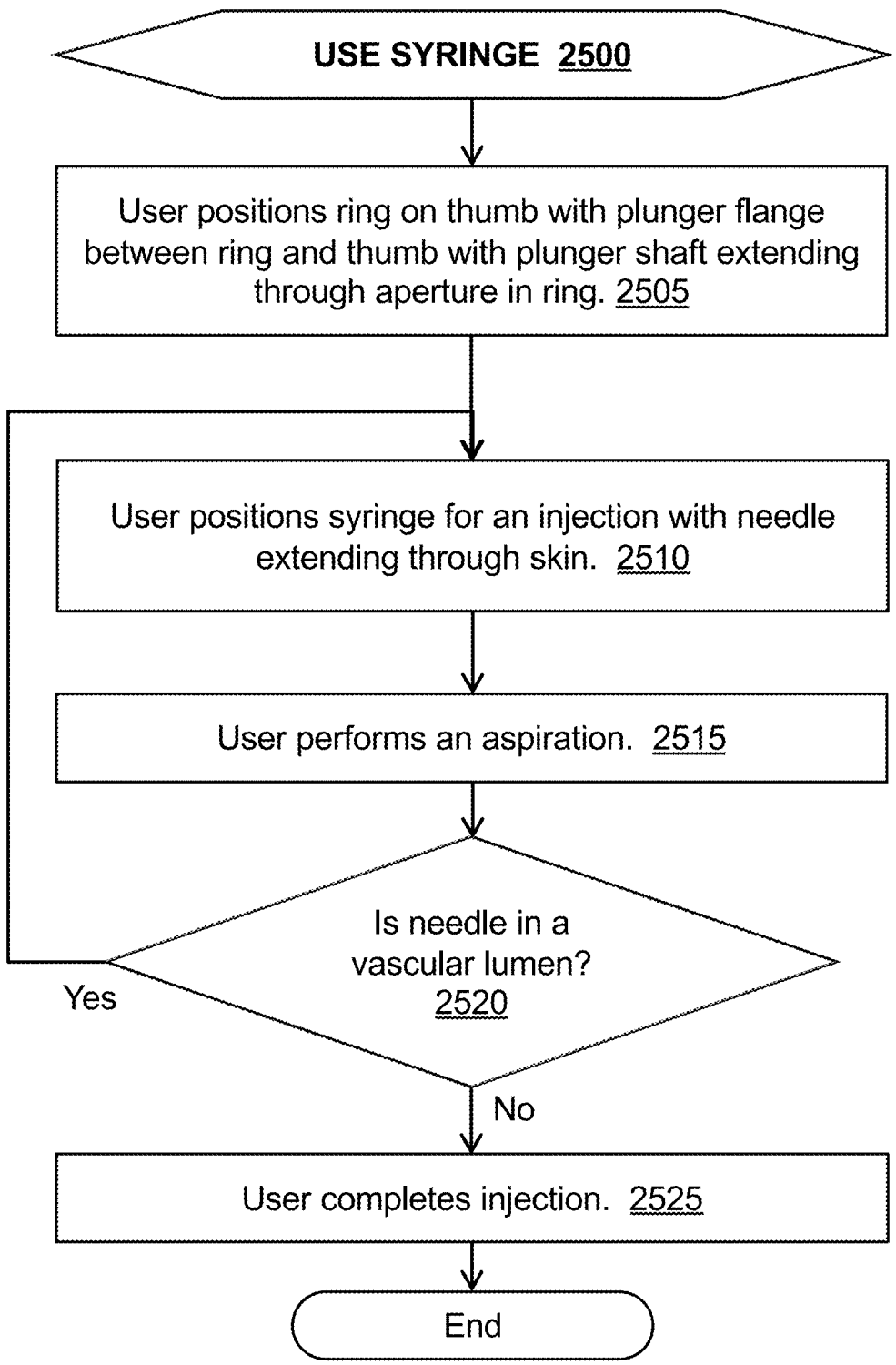
FIG. 25 is a representative flowchart for a process for using a ring for fastening a plunger to a user in accordance with some example embodiments of the disclosure.

Turning now to FIG. 25, this figure illustrates a flowchart for an example process 2500 for using a ring 100 for fastening a plunger 21 to a user 5 according to some embodiments of the disclosure. The flowchart describes the example of operating a plunger 21 of a syringe 27 during a hypodermic injection, without limitation.

Certain steps in process 2500, as well as in the other processes and methods disclosed or taught herein, may naturally need to precede others to achieve desirable functionality. However, the disclosure is not limited to the order of the steps described if such order or sequence does not adversely alter functionality to the extent of rendering the technology inoperable or nonsensical. That is, it is recognized that some steps may be performed before or after other steps or in parallel with other steps without departing from the scope and spirit of the disclosure.

Referring now to the representative flowchart of FIG. 25, an example process 2500 will be further described with example reference to the embodiment illustrated by FIG. 1. Process 2500 can further be practiced with various other embodiments supported by the present disclosure. Accordingly, it will be appreciated that process 2500 can operate with many embodiments and applications, without limitation. Moreover, one of ordinary skill in the art having benefit of this disclosure will be able to practice many variations of process 2500 as may be appropriate for various applications and embodiments.

At block 2505 of process 2500 the user 5 positions the ring 100 on the user's thumb 30 with the flange 22 of the plunger 21 positioned between the ring 100 and the thumb 30. The shaft 23 of the plunger 21 extends through the slot 10 in the ring 100, the slot 10 being an example embodiment of an aperture.

At block 2510 of process 2500, the user 5 positions the syringe 27 for an injection, with the needle 25 extending through the skin 41 of a patient 50. Skin 41 can comprise the patient's face in some examples.

At block 2515 of process 2500, the user 5 aspirates the syringe 27 by retracting the plunger 21. With the ring 100 fastening the plunger 21 to the user's thumb 30, the user 5 may conduct the aspiration with just one hand operating the syringe 27. The user's other hand can be free to steady the patient 50, for example.

At inquiry block 2520, a determination is made as to whether the distal port 88 of the needle 25 of the syringe 27 is positioned in a vascular lumen based on whether the user 5 observes blood entering the syringe 27 as a result of the aspiration.

If the user 5 does not observe blood, the user 5 proceeds with and completes the injection, and process 2500 ends. Completing the injection can comprise injection of dermal filler in some example embodiments.

If, on the other hand, the user 5 observes blood and determines at block 2520 that the syringe 27 is in a vascular lumen, the user withdraws the needle from the patient without completing an injection. Process 2500 branches to block 2510, and the user 5 repositions the syringe 27 to a new location. Process 2500 iterates until finding a suitable location for the injection, at which time the injection is completed.

Technology useful for moving a plunger with dexterity or precision has been described. From the description, it will be appreciated that an embodiment of the disclosure overcomes limitations of the prior art. Those skilled in the art will appreciate that the technology is not limited to any specifically discussed application or implementation and that the embodiments described herein are illustrative and not restrictive. Furthermore, the particular features, structures, or characteristics that are set forth may be combined in any suitable manner in one or more embodiments based on this disclosure and ordinary skill. Those of ordinary skill having benefit of this disclosure can make, use, and practice a wide range of embodiments via combining the disclosed features and elements in many permutations without undue experimentation. This disclosure not only includes the illustrated and described embodiments, but also provides a rich and detailed roadmap for creating many additional embodiments using the various disclosed technologies, elements, features, and their equivalents. From the description of the example embodiments, equivalents of the elements shown herein will suggest themselves to those skilled in the art, and ways of constructing other embodiments will appear to practitioners of the art. Therefore, the scope of the technology is to be limited only by the appended claims.

What is claimed is:

1. An apparatus for fastening a plunger of a hypodermic syringe to a thumb of a medical practitioner, the apparatus comprising
 a ring that is configured to extend at least partially around the thumb of the medical practitioner and that comprises:
  a distal aperture sized to receive a first portion of the thumb;
  a proximal aperture sized to receive a second portion of the thumb that is proximal to the first portion of the thumb, wherein the proximal aperture is enlarged relative to the distal aperture; and
  a section extending longitudinally from the distal aperture to the proximal aperture and circumscribing an interior space in which the thumb is disposed when the ring is worn on the thumb, the section comprising:
   a first corner extending longitudinally from the distal aperture to the proximal aperture;
   a second corner extending longitudinally from the distal aperture to the proximal aperture; and
   a floor that extends laterally from the first corner to the second corner, that extends longitudinally from the distal aperture to the proximal aperture, and that comprises an interior surface facing the interior space,
  wherein the interior surface of the floor has a shape that slopes upward from the proximal aperture to the distal aperture,
  wherein a slot is formed in the floor and is sized to receive a shaft of the plunger and to impede passage of a thumb rest of the plunger, the slot comprising:
   a mouth that is disposed adjacent the distal aperture and that narrows with increasing distance from the distal aperture;
   a closed end that is disposed between the mouth and the proximal aperture; and
   a region that is disposed between the mouth and the closed end and that is narrow relative to the mouth and the closed end,
  wherein the mouth of the slot is distal to the region of the slot and is distal to the closed end of the slot, and
  wherein the mouth of the slot is bent into the interior space.

2. The apparatus of claim 1, wherein the floor comprises a crease that is distal to the closed end of the slot and that is distal to the region of the slot,
 wherein the crease extends into the slot on opposing lateral sides of the slot and comprises a bend in the floor where the mouth of the slot is bent into the interior space, and
 wherein distal to the crease, the mouth of the slot projects into the interior space.

3. The apparatus of claim 1, wherein the floor comprises:
 a first distal edge disposed adjacent the distal aperture on a first lateral side of the slot;
 a second distal edge disposed adjacent the distal aperture on a second lateral side of the slot that opposes the first lateral side of the slot;
 a first area that extends from the first distal edge to the slot on the first lateral side of the slot; and a second area that extends from the second distal edge to the slot on the second lateral side of the slot, wherein the first and second areas of the floor are bent into the interior space and form the mouth of the slot.

4. The apparatus of claim 3, wherein the first area of the floor is bent into the interior space along a first line that extends from the first distal edge to the slot, and wherein the second area of the floor is bent into the interior space along a second line that extends from the second distal edge to the slot.

5. The apparatus of claim 4, wherein the first line and the second line comprise crease lines.

6. The apparatus of claim 4, wherein the first line and the second line converge.

7. The apparatus of claim 1, wherein the interior surface of the floor is curved longitudinally between the proximal aperture and the distal aperture in correspondence with longitudinal curvature of a palmar surface of the thumb that extends distally from an interphalangeal joint of the thumb.

8. The apparatus of claim 1, wherein the ring comprises plastic material.

9. The apparatus of claim 1, further comprising the hypodermic syringe and a dermal filler disposed in the hypodermic syringe.

10. An apparatus for aiding usage of a syringe, the apparatus comprising a ring that comprises:
   a distal aperture;
   a proximal aperture that is longitudinally displaced from the distal aperture and that is larger than the distal aperture; and
   a section extending longitudinally from the distal aperture to the proximal aperture and at least partially circumscribing an interior space of the ring,
wherein the section comprises a floor extending from the distal aperture to the proximal aperture, the floor comprising:
   a slot that is formed in the floor and comprises:
      a mouth that is disposed adjacent the distal aperture and that narrows with increasing distance from the distal aperture;
      an end that is disposed between the mouth and the proximal aperture and that comprises a curved outline; and
      a region that is disposed between the mouth and the end and that is narrow relative to the mouth and the end,
      wherein the mouth of the slot is bent into the interior space and projects into the interior space; and
   an interior surface that faces the interior space and that slopes upward from the proximal aperture to the distal aperture.

11. The apparatus of claim 10, wherein the floor comprises:
   a first distal edge disposed adjacent the distal aperture on a first lateral side of the slot;
   a second distal edge disposed adjacent the distal aperture on a second lateral side of the slot that opposes the first lateral side of the slot;
   a first area that extends from the first distal edge to the slot on the first lateral side of the slot; and
   a second area that extends from the second distal edge to the slot on the second lateral side of the slot,
   wherein the first and second areas of the floor are bent into the interior space and comprise the mouth of the slot.

12. The apparatus of claim 10, wherein the ring is a unitary piece of malleable material.

13. The apparatus of claim 10, wherein the ring is operative to fasten a flange of a plunger of a hypodermic syringe to a thumb of a medical practitioner for one-handed aspiration, wherein the end of the slot is configured to retain the flange between the floor and the thumb during said one-handed aspiration, and wherein the floor is contoured to maintain pressure between the thumb and the flange during said one-handed aspiration, the interior surface of the floor curving longitudinally in correspondence with anatomy of a palmar surface of the thumb that is distal to an interphalangeal joint of the thumb.

14. A method comprising:
providing a system that comprises:
   a barrel that extends along an axis and that comprises a proximal opening and a distal opening; and
   a plunger that extends along the axis and that comprises a shaft and a flange disposed at an end of the shaft,
   wherein the flange is disposed outside the barrel on the axis and the shaft extends from the flange into the barrel through the proximal opening and along the axis towards the distal opening;
disposing the flange between a finger and a ring, wherein the shaft extends through an aperture of the ring and a portion of the ring adjoins the flange;
positioning the system; and
retracting the plunger by moving the finger along the axis away from the barrel of the positioned system, wherein the moving finger applies force to the ring, wherein the portion of the ring translates the applied force to the flange, and wherein the flange translates the applied force to the shaft,
wherein the ring comprises:
   a distal aperture;
   a proximal aperture that is longitudinally displaced from the distal aperture and that is larger than the distal aperture; and
   a section extending longitudinally from the distal aperture to the proximal aperture and at least partially circumscribing an interior space of the ring,
wherein the section comprises a floor extending from the distal aperture to the proximal aperture, the floor comprising:
   a slot that is formed in the floor and comprises:
      a mouth that is disposed adjacent the distal aperture and that narrows with increasing distance from the distal aperture;
      an end that is disposed between the mouth and the proximal aperture and that comprises a curved outline; and
      a region that is disposed between the mouth and the end and that is narrow relative to the mouth and the end,
      wherein the mouth of the slot is bent into the interior space and projects into the interior space; and
   an interior surface that faces the interior space and that slopes upward from the proximal aperture to the distal aperture,
wherein the slot comprises said aperture of the ring, and wherein the portion of the ring comprises the interior surface of the floor of the ring.

15. The method of claim 14, wherein said disposing of the flange between the finger and the ring comprises:
   the steps of:
      disposing a distal portion of the plunger in the slot; and disposing the finger in the ring while the distal portion of the plunger is disposed in the slot; or the steps of:
- disposing the finger in the ring; and
- disposing a distal portion of the plunger in the slot while the finger is disposed in the ring.

16. The method of claim 14, wherein the system comprises a hypodermic syringe and further comprises dermal filler housed in the hypodermic syringe,
- wherein positioning the system comprises inserting a needle of the hypodermic syringe into a facial area of a subject,
- wherein retracting the plunger comprises aspirating to determine whether a distal port of the needle is disposed in a vascular lumen, and
- wherein the method further comprises:
  - responsive to determining that the distal port of the needle is not disposed in a vascular lumen, injecting the dermal filler by manually advancing the plunger into the barrel.

17. The method of claim 14, wherein the ring comprises a first end and a second end, and
- wherein the ring extends clockwise from the slot to the first end and counterclockwise from the slot to the second end.

18. The method of claim 14, wherein the finger is a thumb that comprises a friction ridge region, and
- wherein said disposing the flange between the finger and the ring comprises
  - disposing the flange between the friction ridge region and the ring with deformation of the friction ridge region pressing the flange against the interior surface of the floor of the ring that faces the friction ridge region.

19. The method of claim 18, wherein said deformation of the friction ridge region presses the flange against the interior surface of the floor of the ring throughout said retraction of the plunger.

20. The method of claim 18, further comprising strapping the ring onto the thumb.

\* \* \* \* \*